(12) United States Patent
Barrus et al.

(10) Patent No.: US 7,438,703 B2
(45) Date of Patent: Oct. 21, 2008

(54) SAFETY SHIELD FOR MEDICAL NEEDLES

(75) Inventors: Roy L. Barrus, Centerville, UT (US); David L. Thorne, Kaysville, UT (US); Charles V. Owen, Highland, UT (US); Donald D. Solomon, Ogden, UT (US); F. Mark Ferguson, Salt Lake City, UT (US); Michael Thorne, Bountiful, UT (US); Stephen Brown, Roy, UT (US); Gale H. Thorne, Jr., Bountiful, UT (US)

(73) Assignee: Tyco Healthcare Group LP, Mansfield, MA (US)

( * ) Notice: Subject to any disclaimer, the term of this patent is extended or adjusted under 35 U.S.C. 154(b) by 350 days.

(21) Appl. No.: 10/016,276

(22) Filed: Dec. 6, 2001

(65) Prior Publication Data

US 2002/0072716 A1 Jun. 13, 2002

Related U.S. Application Data

(63) Continuation-in-part of application No. 09/892,593, filed on Jun. 27, 2001, now Pat. No. 7,198,618.

(60) Provisional application No. 60/296,968, filed on Jun. 8, 2001, provisional application No. 60/254,506, filed on Dec. 8, 2000.

(51) Int. Cl.
*A61M 5/32* (2006.01)

(52) U.S. Cl. ........................... 604/192; 128/919

(58) Field of Classification Search .............. 604/110, 604/164.78, 192, 197, 198, 263, 272; 128/919
See application file for complete search history.

(56) References Cited

U.S. PATENT DOCUMENTS

| | | | |
|---|---|---|---|
| 1,779,451 A | 10/1930 | Sponsel | |
| 2,559,474 A | 7/1951 | Son | 128/215 |
| 2,700,385 A | 1/1955 | Ortiz | 128/215 |
| 2,836,942 A | 6/1958 | Miskel | 53/25 |
| 2,854,976 A | 10/1958 | Heydrich | 128/221 |
| 2,953,243 A | 9/1960 | Roehr | 206/43 |
| 3,021,942 A | 2/1962 | Hamilton | 206/43 |
| 3,073,307 A | 1/1963 | Stevens | 128/221 |
| 3,074,542 A | 1/1963 | Myerson et al. | 206/43 |
| 3,255,873 A | 6/1966 | Speelman | 206/56 |
| 3,294,231 A | 12/1966 | Vanderbeck | 206/63 |

(Continued)

FOREIGN PATENT DOCUMENTS

EP 0 144 483 A2 6/1985

(Continued)

*Primary Examiner*—Catherine S. Williams

(57) ABSTRACT

A safety shield apparatus is disclosed which includes a needle having a distal portion defining a longitudinal axis which is angularly displaced relative to a longitudinal axis defined by a proximal portion of the needle. A shield is mounted with the needle and extensible, via a tubular needle guide movable along the needle, between a retracted position and an extended position. The apparatus may include a needle hub configured to support the proximal portion of the needle. The needle hub can include an appendage which may have at least one opening to facilitate manipulation thereof. A distal end of the shield can be attached to a planar contact surface. The shield may also include a latch engageable with the needle.

4 Claims, 35 Drawing Sheets

U.S. PATENT DOCUMENTS

| | | | | |
|---|---|---|---|---|
| 3,323,523 A | 6/1967 | Scislowicz et al. | ........... | 128/214 |
| 3,329,146 A | 7/1967 | Waldman, Jr. | ............... | 128/221 |
| 3,333,682 A | 8/1967 | Burke | ........................ | 206/43 |
| 3,367,488 A | 2/1968 | Hamilton | .................... | 206/63 |
| 3,485,239 A | 12/1969 | Vanderbeck | ................ | 128/218 |
| 3,537,452 A | 11/1970 | Wilks | ........................ | 128/214 |
| 3,587,575 A | 6/1971 | Lichtenstein | ................ | 128/215 |
| 3,610,240 A | 10/1971 | Harautuneian | .............. | 128/214 |
| 3,658,061 A | 4/1972 | Hall | ........................... | 128/214 |
| 3,685,645 A | 8/1972 | Kawaguchi | | |
| 3,828,775 A | 8/1974 | Armel | ........................ | 128/218 |
| 3,840,008 A | 10/1974 | Noiles | ........................ | 128/221 |
| 3,890,971 A | 6/1975 | Leeson et al. | ................ | 128/218 |
| 3,904,033 A | 9/1975 | Haerr | ......................... | 206/349 |
| 3,918,446 A | 11/1975 | Buttaravoli | | |
| 3,934,722 A | 1/1976 | Goldberg | .................... | 206/365 |
| 3,968,876 A | 7/1976 | Brookfield | .................. | 206/365 |
| 4,040,419 A | 8/1977 | Goldman | .................... | 128/215 |
| 4,106,621 A | 8/1978 | Sorenson | .................... | 206/365 |
| 4,113,090 A | 9/1978 | Carstens | ..................... | 206/365 |
| 4,139,009 A | 2/1979 | Alvarez | ...................... | 128/218 |
| 4,175,008 A | 11/1979 | White | ........................ | 435/295 |
| 4,270,536 A | 6/1981 | Lemelson | .................... | 128/218 |
| 4,300,678 A | 11/1981 | Gyure et al. | ................. | 206/364 |
| 4,375,849 A | 3/1983 | Hanifl | ......................... | 206/366 |
| 4,430,082 A | 2/1984 | Schwabacher | .............. | 604/263 |
| 4,592,744 A | 6/1986 | Jagger et al. | ................. | 604/192 |
| 4,634,428 A | 1/1987 | Cuu | ........................... | 604/110 |
| 4,643,722 A | 2/1987 | Smith, Jr. | .................... | 604/192 |
| 4,659,330 A | 4/1987 | Nelson et al. | ............... | 604/192 |
| 4,664,259 A | 5/1987 | Landis | ........................ | 206/365 |
| 4,664,654 A | 5/1987 | Strauss | ........................ | 604/198 |
| 4,681,567 A | 7/1987 | Masters et al. | .............. | 604/198 |
| 4,690,675 A | 9/1987 | Katz | | |
| 4,695,274 A | 9/1987 | Fox | ............................ | 604/198 |
| 4,702,738 A | 10/1987 | Spencer | ...................... | 604/198 |
| 4,723,943 A | 2/1988 | Spencer | ...................... | 604/198 |
| 4,728,320 A | 3/1988 | Chen | ......................... | 604/110 |
| 4,728,321 A | 3/1988 | Chen | ......................... | 604/110 |
| 4,731,059 A | 3/1988 | Wanderer et al. | ........... | 604/192 |
| 4,735,311 A | 4/1988 | Lowe et al. | .................. | 206/365 |
| 4,735,618 A * | 4/1988 | Hagen | ........................ | 604/192 |
| 4,737,144 A | 4/1988 | Choksi | ........................ | 604/198 |
| 4,738,663 A | 4/1988 | Bogan | ........................ | 604/198 |
| 4,743,233 A | 5/1988 | Schneider | ................... | 604/192 |
| 4,747,836 A | 5/1988 | Luther | ......................... | 604/198 |
| 4,747,837 A | 5/1988 | Hauck | ........................ | 604/198 |
| 4,772,272 A | 9/1988 | McFarland | .................. | 604/198 |
| 4,778,453 A | 10/1988 | Lopez | ........................ | 604/110 |
| 4,781,697 A | 11/1988 | Slaughter | ................... | 604/192 |
| 4,782,841 A | 11/1988 | Lopez | ........................ | 128/164 |
| 4,790,828 A | 12/1988 | Dombrowski et al. | ........ | 604/198 |
| 4,795,432 A | 1/1989 | Karczmer | ................... | 604/110 |
| 4,795,443 A | 1/1989 | Permenter et al. | ........... | 604/198 |
| 4,801,295 A | 1/1989 | Spencer | ...................... | 604/198 |
| 4,804,372 A | 2/1989 | Laico et al. | .................. | 604/198 |
| 4,813,426 A | 3/1989 | Haber et al. | ................. | 128/763 |
| 4,816,022 A | 3/1989 | Poncy | ........................ | 604/198 |
| 4,816,024 A | 3/1989 | Sitar et al. | ................... | 604/192 |
| 4,819,659 A | 4/1989 | Sitar | ........................... | 128/764 |
| 4,820,277 A | 4/1989 | Norelli | ........................ | 604/192 |
| 4,826,490 A | 5/1989 | Byrne et al. | ................. | 604/198 |
| 4,826,491 A | 5/1989 | Schramm | .................... | 604/198 |
| 4,838,871 A | 6/1989 | Luther | ......................... | 604/192 |
| 4,840,619 A | 6/1989 | Hughes | ....................... | 604/187 |
| 4,842,587 A | 6/1989 | Poncy | ........................ | 604/198 |
| 4,846,796 A | 7/1989 | Carrell et al. | ................. | 604/110 |
| 4,846,811 A | 7/1989 | Vanderhoof | ................. | 604/263 |
| 4,850,968 A | 7/1989 | Romano | ...................... | 604/110 |
| 4,850,976 A | 7/1989 | Heinrich et al. | .............. | 604/192 |
| 4,850,977 A | 7/1989 | Bayless | ....................... | 604/198 |
| 4,850,978 A | 7/1989 | Dudar et al. | ................. | 604/201 |
| 4,850,994 A | 7/1989 | Zerbst et al. | ................. | 604/198 |
| 4,850,996 A | 7/1989 | Cree | ........................... | 604/198 |
| 4,858,607 A | 8/1989 | Jordan et al. | ................ | 128/314 |
| 4,863,434 A | 9/1989 | Bayless | ....................... | 604/198 |
| 4,863,435 A | 9/1989 | Sturman et al. | .............. | 604/198 |
| 4,863,436 A | 9/1989 | Glick | .......................... | 604/198 |
| 4,867,172 A | 9/1989 | Haber et al. | ................. | 128/763 |
| 4,867,746 A | 9/1989 | Dufresne | .................... | 604/192 |
| 4,872,552 A | 10/1989 | Unger | ........................ | 206/365 |
| 4,874,382 A | 10/1989 | Lindemann et al. | ......... | 604/195 |
| 4,874,383 A | 10/1989 | McNaughton | ............. | 604/198 |
| 4,874,384 A | 10/1989 | Nunez | ........................ | 601/198 |
| 4,883,469 A | 11/1989 | Glazier | ....................... | 604/192 |
| 4,886,503 A | 12/1989 | Miller | ........................ | 604/192 |
| 4,887,998 A | 12/1989 | Martin et al. | ................ | 604/110 |
| 4,888,001 A | 12/1989 | Schoenberg | ................. | 604/162 |
| 4,892,107 A | 1/1990 | Haber | ........................ | 128/763 |
| 4,892,521 A | 1/1990 | Laico et al. | .................. | 604/192 |
| 4,898,589 A * | 2/1990 | Dolgin et al. | ................. | 604/198 |
| 4,900,309 A | 2/1990 | Netherton et al. | ........... | 604/192 |
| 4,904,244 A | 2/1990 | Harsh et al. | .................. | 604/187 |
| 4,911,694 A | 3/1990 | Dolan | ......................... | 604/198 |
| 4,911,706 A | 3/1990 | Levitt | ......................... | 604/198 |
| 4,927,018 A | 5/1990 | Yang et al. | .................. | 206/365 |
| 4,929,241 A | 5/1990 | Kulli | .......................... | 604/263 |
| 4,935,012 A | 6/1990 | Magre et al. | ................. | 604/192 |
| 4,935,013 A | 6/1990 | Haber et al. | ................. | 604/192 |
| 4,936,830 A | 6/1990 | Verlier | ........................ | 604/110 |
| 4,944,397 A | 7/1990 | Miller | ........................ | 206/365 |
| 4,944,731 A | 7/1990 | Cole | ........................... | 604/192 |
| 4,950,249 A | 8/1990 | Jagger et al. | ................. | 604/192 |
| 4,950,250 A | 8/1990 | Haber et al. | ................. | 604/192 |
| 4,966,589 A * | 10/1990 | Kaufman | .................... | 604/174 |
| 4,978,344 A | 12/1990 | Dombrowski et al. | ........ | 604/198 |
| 4,982,842 A | 1/1991 | Hollister | ..................... | 206/365 |
| 4,985,021 A | 1/1991 | Straw et al. | .................. | 604/198 |
| 4,994,041 A | 2/1991 | Dombrowski et al. | ........ | 604/164 |
| 5,000,744 A | 3/1991 | Hoffman et al. | ............. | 604/232 |
| 5,015,240 A | 5/1991 | Soproni et al. | ............... | 604/192 |
| 5,057,089 A | 10/1991 | Greco | ........................ | 604/198 |
| 5,059,180 A | 10/1991 | McLees | ....................... | 604/110 |
| 5,092,851 A | 3/1992 | Ragner | ....................... | 604/192 |
| 5,108,379 A | 4/1992 | Dolgin et al. | ................. | 604/198 |
| RE34,045 E | 8/1992 | McFarland | .................. | 604/198 |
| 5,135,509 A | 8/1992 | Olliffee | ....................... | 604/192 |
| 5,139,489 A | 8/1992 | Hollister | ..................... | 604/192 |
| 5,147,303 A | 9/1992 | Martin | ........................ | 604/110 |
| 5,154,285 A | 10/1992 | Hollister | ..................... | 206/365 |
| 5,176,655 A | 1/1993 | McCormick et al. | ......... | 604/198 |
| 5,176,656 A | 1/1993 | Bayless | ....................... | 604/198 |
| 5,193,552 A | 3/1993 | Columbus et al. | ........... | 128/760 |
| 5,195,983 A | 3/1993 | Boese | ........................ | 604/192 |
| 5,209,739 A | 5/1993 | Talalay | ....................... | 604/195 |
| 5,215,525 A | 6/1993 | Sturman | | |
| 5,232,454 A | 8/1993 | Hollister | ..................... | 604/192 |
| 5,232,455 A | 8/1993 | Hollister | ..................... | 604/192 |
| 5,242,417 A | 9/1993 | Paudler | ....................... | 604/192 |
| 5,242,418 A | 9/1993 | Weinstein | ................... | 604/192 |
| 5,246,427 A | 9/1993 | Sturman et al. | .............. | 604/192 |
| 5,246,428 A | 9/1993 | Falknor | ....................... | 604/198 |
| 5,250,031 A * | 10/1993 | Kaplan et al. | ................ | 604/110 |
| 5,254,099 A | 10/1993 | Kuracina et al. | ............. | 604/198 |
| 5,256,152 A * | 10/1993 | Marks | ........................ | 604/198 |
| 5,256,153 A | 10/1993 | Hake | ........................... | 604/198 |
| 5,277,311 A | 1/1994 | Hollister | ..................... | 206/365 |
| 5,290,255 A | 3/1994 | Vallelunga et al. | .......... | 604/197 |
| 5,304,137 A | 4/1994 | Fluke | ......................... | 604/110 |
| 5,312,369 A | 5/1994 | Arcusin et al. | ............... | 604/192 |
| 5,334,158 A | 8/1994 | McLees | ....................... | 604/110 |
| 5,348,544 A | 9/1994 | Sweeney et al. | ............. | 604/192 |
| 5,356,392 A | 10/1994 | Firth et al. | ................... | 604/198 |
| 5,403,283 A | 4/1995 | Luther | ........................ | 604/164 |

| | | | |
|---|---|---|---|
| 5,403,286 A | 4/1995 | Lockwood, Jr. | 604/110 |
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |
| 5,423,766 A | 6/1995 | Di Cesare | 604/192 |
| 5,425,720 A | 6/1995 | Rogalsky et al. | 604/198 |
| 5,445,618 A * | 8/1995 | Adobbati | 604/192 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,490,841 A | 2/1996 | Landis | 604/110 |
| 5,498,243 A | 3/1996 | Vallelunga et al. | 604/197 |
| 5,531,694 A | 7/1996 | Clemens et al. | 604/110 |
| 5,531,704 A | 7/1996 | Knotek | |
| 5,533,980 A | 7/1996 | Sweeney et al. | 604/192 |
| 5,536,240 A * | 7/1996 | Edwards et al. | 604/22 |
| 5,538,508 A | 7/1996 | Steyn | 604/192 |
| 5,542,927 A | 8/1996 | Thorne et al. | 604/110 |
| 5,549,568 A | 8/1996 | Shields | 604/192 |
| 5,549,570 A | 8/1996 | Rogalsky | 604/198 |
| 5,549,708 A | 8/1996 | Thorne et al. | 604/198 |
| 5,562,629 A | 10/1996 | Haughton et al. | 604/158 |
| 5,562,631 A | 10/1996 | Bogert | 604/164 |
| 5,573,510 A | 11/1996 | Isaacson | 604/158 |
| 5,584,816 A | 12/1996 | Gyure et al. | 604/192 |
| 5,584,818 A | 12/1996 | Morrison | 604/197 |
| 5,599,318 A | 2/1997 | Sweeney et al. | 604/263 |
| 5,611,782 A | 3/1997 | Haedt | 604/198 |
| 5,643,220 A | 7/1997 | Cosme | 604/192 |
| 5,672,161 A | 9/1997 | Allen et al. | 604/263 |
| 5,695,474 A | 12/1997 | Daugherty | 604/162 |
| 5,695,477 A | 12/1997 | Sfikas | 604/241 |
| 5,700,249 A | 12/1997 | Jenkins | 604/263 |
| 5,735,827 A | 4/1998 | Adwers et al. | 604/263 |
| 5,738,665 A | 4/1998 | Caizza et al. | 604/198 |
| 5,746,718 A | 5/1998 | Steyn | 604/192 |
| 5,746,726 A | 5/1998 | Sweeney et al. | 604/263 |
| 5,755,699 A | 5/1998 | Blecher et al. | 604/198 |
| 5,814,018 A | 9/1998 | Elson et al. | 604/110 |
| 5,817,064 A | 10/1998 | DeMarco et al. | 604/198 |
| 5,823,997 A * | 10/1998 | Thorne | 604/110 |
| 5,843,041 A | 12/1998 | Hake et al. | 604/198 |
| 5,879,330 A * | 3/1999 | Bell | 604/93.01 |
| 5,879,337 A * | 3/1999 | Kuracina et al. | 604/192 |
| 5,910,130 A | 6/1999 | Caizza et al. | 604/110 |
| 5,919,168 A | 7/1999 | Wheeler | 604/198 |
| 5,921,969 A * | 7/1999 | Vallelunga et al. | 604/263 |
| 5,925,020 A | 7/1999 | Nestell | 604/198 |
| 5,951,522 A | 9/1999 | Rosato et al. | 604/177 |
| 5,957,892 A | 9/1999 | Thorne | 604/162 |
| 5,980,488 A | 11/1999 | Thorne | 604/110 |
| 5,997,504 A * | 12/1999 | Bell | 604/164.01 |
| 6,015,397 A | 1/2000 | Elson et al. | 604/192 |
| 6,036,675 A | 3/2000 | Thorne et al. | 604/232 |
| 6,149,629 A | 11/2000 | Wilson et al. | 604/198 |
| 6,171,284 B1 | 1/2001 | Kao et al. | 604/192 |
| RE37,110 E | 3/2001 | Hollister | 206/365 |
| 6,224,576 B1 | 5/2001 | Thorne et al. | 604/198 |
| RE37,252 E | 7/2001 | Hollister | 206/364 |
| 6,254,575 B1 | 7/2001 | Thorne, Jr. et al. | 604/198 |
| 6,280,420 B1 | 8/2001 | Ferguson et al. | 604/198 |
| 6,334,857 B1 | 1/2002 | Hollister et al. | 604/263 |
| 6,582,397 B2 | 6/2003 | Alesi et al. | 604/110 |
| 6,824,530 B2 * | 11/2004 | Wagner et al. | 604/162 |
| 2001/0039401 A1 | 11/2001 | Ferguson et al. | |
| 2002/0004650 A1 | 1/2002 | Kuracina et al. | |
| 2002/0072716 A1 | 6/2002 | Barrus et al. | |
| 2003/0004465 A1 | 1/2003 | Ferguson et al. | |

FOREIGN PATENT DOCUMENTS

| | | |
|---|---|---|
| EP | 0 344 606 A2 | 12/1989 |
| EP | 0 457 477 B1 | 11/1991 |
| EP | 0 485 345 A1 | 5/1992 |
| EP | 0 533 308 A1 | 3/1993 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 0 807 443 A2 | 11/1997 |
| EP | 0 815 888 A2 | 1/1998 |
| EP | 0 815 890 A2 | 1/1998 |
| EP | 0 819 441 A1 | 1/1998 |
| EP | 0 832 659 A2 | 4/1998 |
| EP | 0 832 660 A2 | 4/1998 |
| EP | 1 092 443 A2 | 4/2001 |
| EP | 1 116 493 A1 | 7/2001 |
| FR | 2803529 | 1/2001 |
| GB | 1233302 | 5/1971 |
| GB | 2 283 429 A | 5/1995 |
| GB | 2 369 779 | 6/2002 |
| JP | 10-76007 | 3/1998 |
| JP | 10-127765 | 5/1998 |
| WO | WO 87/07162 | 12/1987 |
| WO | WO 89/07955 | 9/1989 |
| WO | WO 93/17732 | 9/1993 |
| WO | WO 94/19036 | 9/1994 |
| WO | WO 97/31666 | 9/1997 |
| WO | WO 98/07463 | 2/1998 |
| WO | WO 98/10816 | 3/1998 |
| WO | WO 98/11928 | 3/1998 |
| WO | WO 98/13081 | 4/1998 |
| WO | WO 00/16832 | 3/2000 |
| WO | WO 00/38765 | 7/2000 |
| WO | WO 01/32241 A1 | 5/2001 |
| WO | WO 01/32244 A1 | 5/2001 |

* cited by examiner

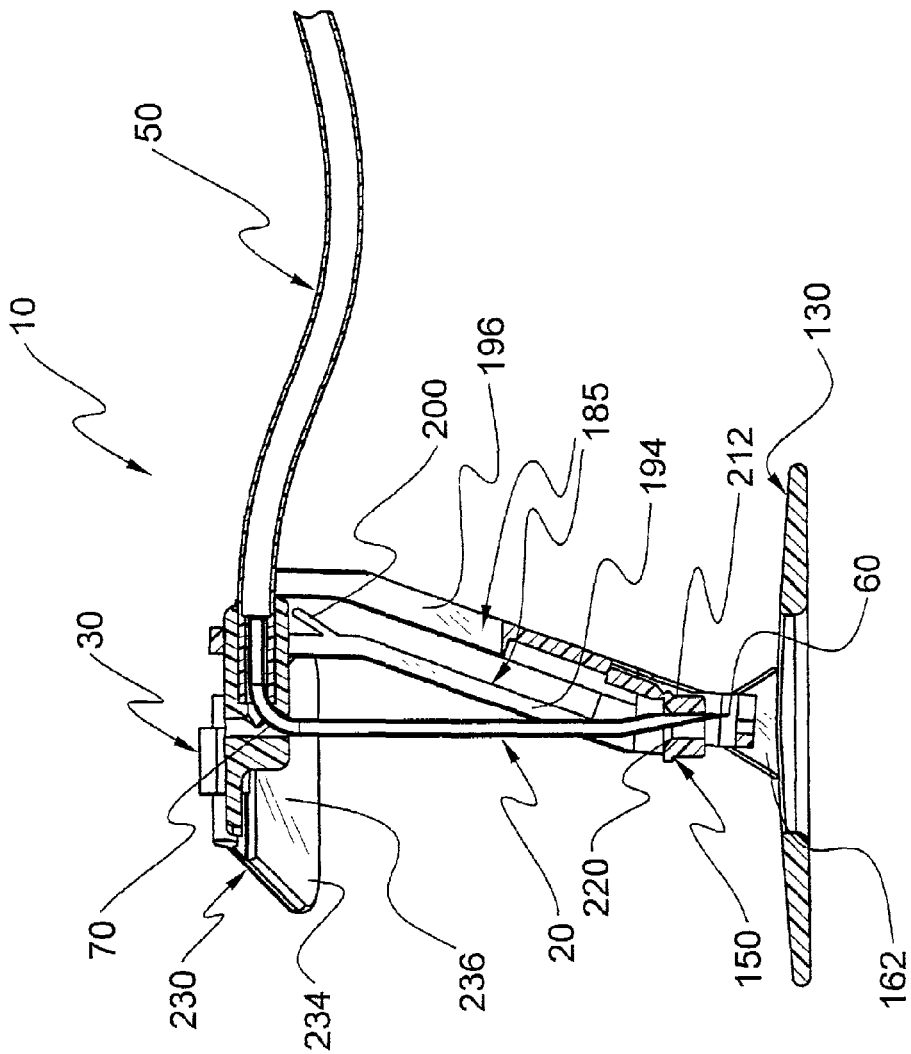

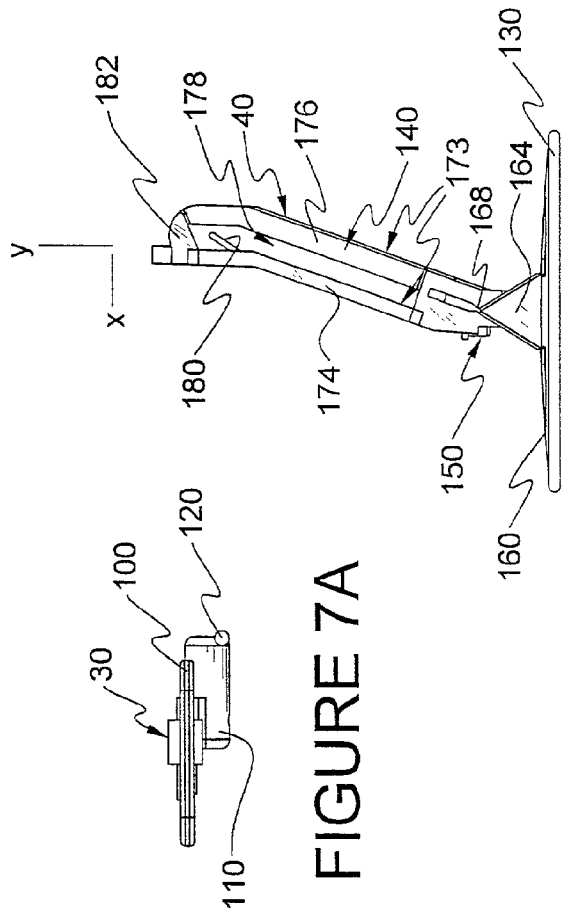
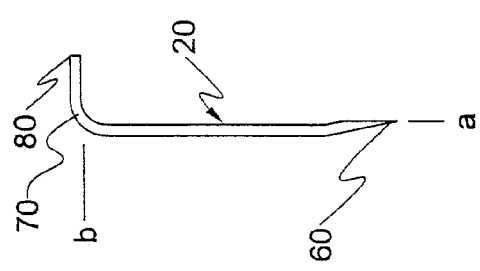
FIGURE 7A
FIGURE 7B
FIGURE 7C
FIGURE 7

SAFETY SHIELD FOR MEDICAL NEEDLES

CROSS-REFERENCE TO RELATED APPLICATIONS

This patent application is a continuation-in-part of U.S. patent application Ser. No. 09/892,593, filed in the USPTO on Jun. 27, 2001 now U.S. Pat. No. 7,198,618 by Ferguson et al., which is a continuation-in-part of U.S. Utility Patent Application Ser. No. 09/433,449, filed Nov. 4, 1999, U.S. Utility Patent Application Ser. No. 09/434,036, filed Nov. 4, 1999, and U.S. Utility Patent Application Ser. No. 09/619,190, filed Jul. 19, 2000, which claims benefit of U.S. Provisional Application Ser. No. 60/254,506 filed in the USPTO on Dec. 8, 2000 by Thorne et al., U.S. Provisional Application Ser. No. 60/275,810, filed Mar. 14, 2001, U.S. Provisional Application Ser. No. 60/275,886, filed Mar. 14, 2001 and U.S. Provisional Application Ser. No. 60/296,968 filed in the USPTO on Jun. 8, 2001 by Barrus et al., the entire contents of each of these applications being hereby incorporated by reference herein.

BACKGROUND

1. Technical Field

The present disclosure generally relates to safety shields for medical needles, and more particularly, to safety shields that are extensible to prevent hazardous exposure to a port access medical needle.

2. Description of the Related Art

Cross-contamination and infection from potentially fatal diseases transmitted by inadvertent needle sticks have resulted in the development of a wide variety of safety medical needle devices used in the areas of I.V. therapy, phlebotomy, syringes and specialty medical needle devices. These diseases include the HIV virus, several strains of hepatitis and other blood and body fluid borne diseases.

Vascular access ports can be surgically implanted to facilitate removal of bodily fluids, such as, for example, blood for testing. Access ports also provide a temporary site for repeated fluid removal, infusion of intravenous fluids or medication infusion. An access port is typically positioned internally on a body surface of a patient, such as, for example, in the chest or abdomen, to facilitate disposition of a catheter into a blood vessel.

Typically, port access medical needles, such as a Huber needle, are used with the access ports which are implanted for direct vascular communication. Huber needles typically include an angled cannula shaft having a sharpened tip portion oriented at approximately 90 degrees relative to an attachment portion that connects to a fluid source and/or a fluid receptacle. The angular bend in the cannula shaft allows the attachment portion to be secured to the patient while the access port is employed.

Access ports typically include a septum positioned under the surface of the patient's skin, and adapted to receive a Huber needle puncture at a percutaneous insertion site. The septum is conventionally fabricated from a thick elastomeric membrane which facilitates needle penetration and provides an inner chamber for the infusion of medication or removal of bodily fluids.

Huber needles may be particularly difficult to remove from a needle access port which can result in hazardous exposure of the needle to a patient and a clinician. This is due, at least in As part, to the fact that access port septums exhibit forces associated with needle entry and removal, which are much greater than forces normally associated with other medical needle insertion and removal (e.g., with syringes or phlebotomy needles). "Rebound" injuries are typically encountered with Huber needles because of the force required to overcome resistance of the septum of the access port. Further, other factors can contribute to the septum's resistance, such as, for example, the needle tip may become barbed, skin may adhere to the needle shaft, etc.

Attempts at overcoming the above retention and resistive forces may result in a reflexive motion (e.g., a jerk) by the clinician removing the needle at the time of extraction which can contribute to the "rebound" injuries. The reflexive motion may be poorly controlled, oscillatory and, therefore, result in an inadvertent needle stick to the patient and clinician, for example, to a hand which is stabilizing an implanted port. Further, difficulty in removal can force a clinician to make a perpendicular pull, which is transverse to a plane orthogonal to the direction of needle insertion. This can result in injury to the patient and the clinician.

A number of Huber needle safety devices are known. For example, one particular device involves a shield separate from the needle for shielding the needle. These types of devices disadvantageously require manipulation and operation of separate devices for shielding the needle. These devices are also bulky and cumbersome which can affect accuracy of placement during use.

Another known attempt at reducing hazards associated with angled needles is a safety device that includes a collapsible pair of wings engaged by the fingers of a clinician to shield the needle. A drawback of devices of this type is that a narrow surface area presses against a patient's skin during withdrawal, which can cause significant pain and discomfort.

The prior art devices may not adequately and reliably shield port access needles to prevent hazardous exposure. A continuing need exists to overcome the disadvantages and drawbacks of the prior art and provide a more adequate and reliable safety apparatus for angled needle devices which sheaths a needle upon removal from an insertion site. Such a safety apparatus may be actuated without applying substantial transverse forces to the needle during removal, while complementing the current user technique.

Therefore, it would be desirable to have a safety apparatus for port access needle devices that sheaths a needle upon removal from an insertion site. It would be highly desirable if the safety apparatus was actuated without applying substantial transverse forces to the needle during removal.

SUMMARY

Accordingly, a safety apparatus for port access needle devices that adequately and reliably sheaths a needle upon removal from an insertion site is disclosed. The safety apparatus prevents hazardous exposure to the needle while providing dependable performance and increased safety to a patient and clinician during a medical procedure. The safety apparatus may be actuated without applying substantial transverse forces to the needle during removal. One of the advantages of the present disclosure is a safety apparatus through which extracting forces are directed along a longitudinal axis of the needle. Another advantage of the present disclosure is port access medical needle which forms a compact low silhouette about an insertion site while the needle is inserted. Yet another advantage of the present disclosure is a safety apparatus which is efficiently and inexpensively manufactured and assembled. Desirably, the safety apparatus is assembled from two injection molded parts.

Objects and advantages of the present disclosure are set forth in part herein and in part will be obvious therefrom, or may be learned by practice of the present disclosure, which is realized and attained by means of the instrumentalities and combinations pointed out in the appended claims. The apparatus and methods of the present disclosure consist of novel parts, constructions, arrangements, combinations, steps and improvements herein shown and described.

The safety apparatus disclosed permits a retracting force to be applied directly above a needle insertion site and may include an elongated, slender core structure for ease of maneuverability to facilitate needle entry into difficult to access ports or vessels. The safety apparatus can provide shielding of a sharpened tip of a port access medical needle, such as, for example, a Huber needle, having a sharpened tip at one end and firmly affixed within a needle hub at the other end, during withdrawal from an insertion site. Extraction of the needle from the insertion site may require forces significantly greater than forces associated with extracting other medical needles, such as hypodermic syringes or phlebotomy. Thus, the safety apparatus can include a shield assembly having a finger pad for application of restraining forces about the insertion site. The finger pad spreads digitally applied forces to stabilize the implanted portion of the needle.

The shield assembly contains a needle guide through which the needle travels during needle extraction. A shield is hingedly affixed to the shield assembly for articulation along the needle during needle extraction. The sharpened tip of the needle is retracted into the shield assembly, forming a substantially rigid structure of the shield, needle guide, needle hub and needle. A latch may engage the shield assembly to maintain the rigid structure in a protective configuration about the sharpened tip. Thus, the needle is extracted and shielded without applying substantial transverse forces to the needle.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, wherein:

FIG. 4A is a medial side view, in part cross-section, of the safety shield apparatus shown in FIG. 4;

FIG. 7 is a side view of a portion of an angled needle of the safety shield apparatus shown in FIG. 1;

FIG. 7A is a side view of a portion of a needle hub assembly of the safety shield apparatus shown in FIG. 1;

FIG. 7B is a side view of a portion of a shield of the safety shield apparatus shown in FIG. 1;

FIG. 7C is a side view of a portion of a fluid conduit employed with the safety shield apparatus shown in FIG. 1;

DETAILED DESCRIPTION OF THE EXEMPLARY EMBODIMENTS

The exemplary embodiments of the safety shield apparatus and methods of operation disclosed are discussed in terms of medical needles for infusion of intravenous fluids, medication infusion or fluid collection, and more particularly, in terms of port access needle apparatus, employing a needle cannula, that prevent hazardous exposure to the needle cannula, including, for example, inadvertent needle stick. It is contemplated that the safety shield apparatus may also be used for implanted infusion pumps or other similar implanted devices. It is further contemplated that the needle cannula may be shielded during use including storage, transport, fluid infusion and/or collection, subsequent thereto, etc. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids, including, those employed during procedures relating to phlebotomy, digestive, intestinal, urinary, veterinary, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety shield apparatus. According to the present disclosure, the term "clinician" refers to an individual administering an infusion, performing fluid collection, installing or removing a needle cannula from a safety shield apparatus and may include support personnel.

The following discussion includes a description of the safety shield apparatus, followed by a description of the method of operating the safety shield apparatus in accordance with the present disclosure. Reference will now be made in detail to the exemplary embodiments of the disclosure, which are illustrated in the accompanying figures.

Figure 2:
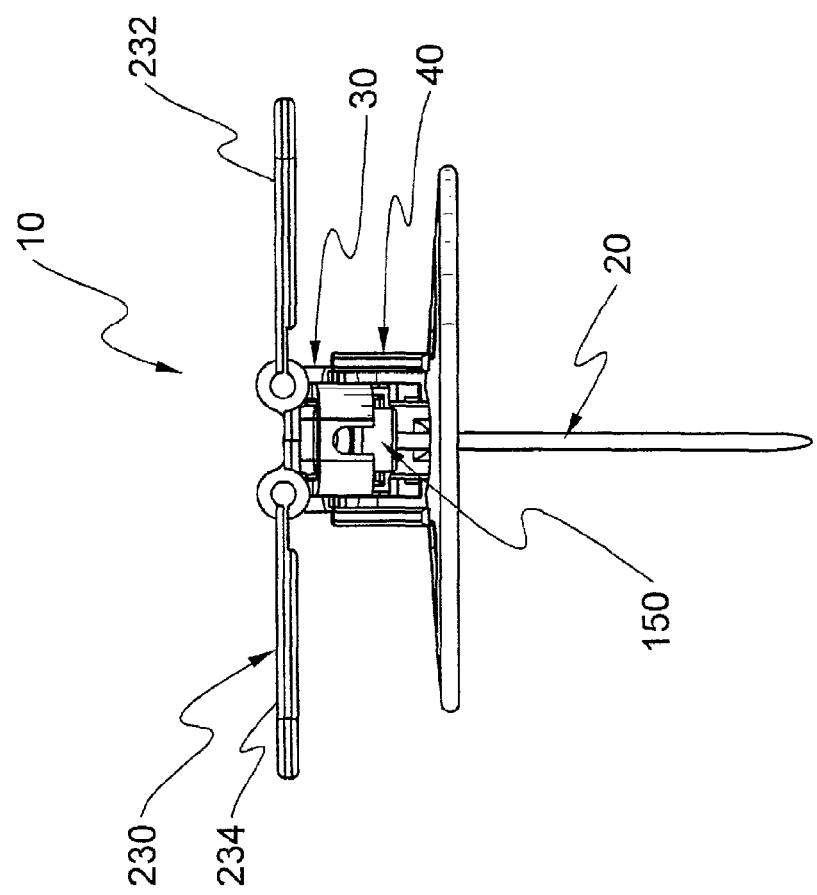
FIG. 2 is a front view of the safety shield apparatus shown in FIG. 1.
Figure 3:
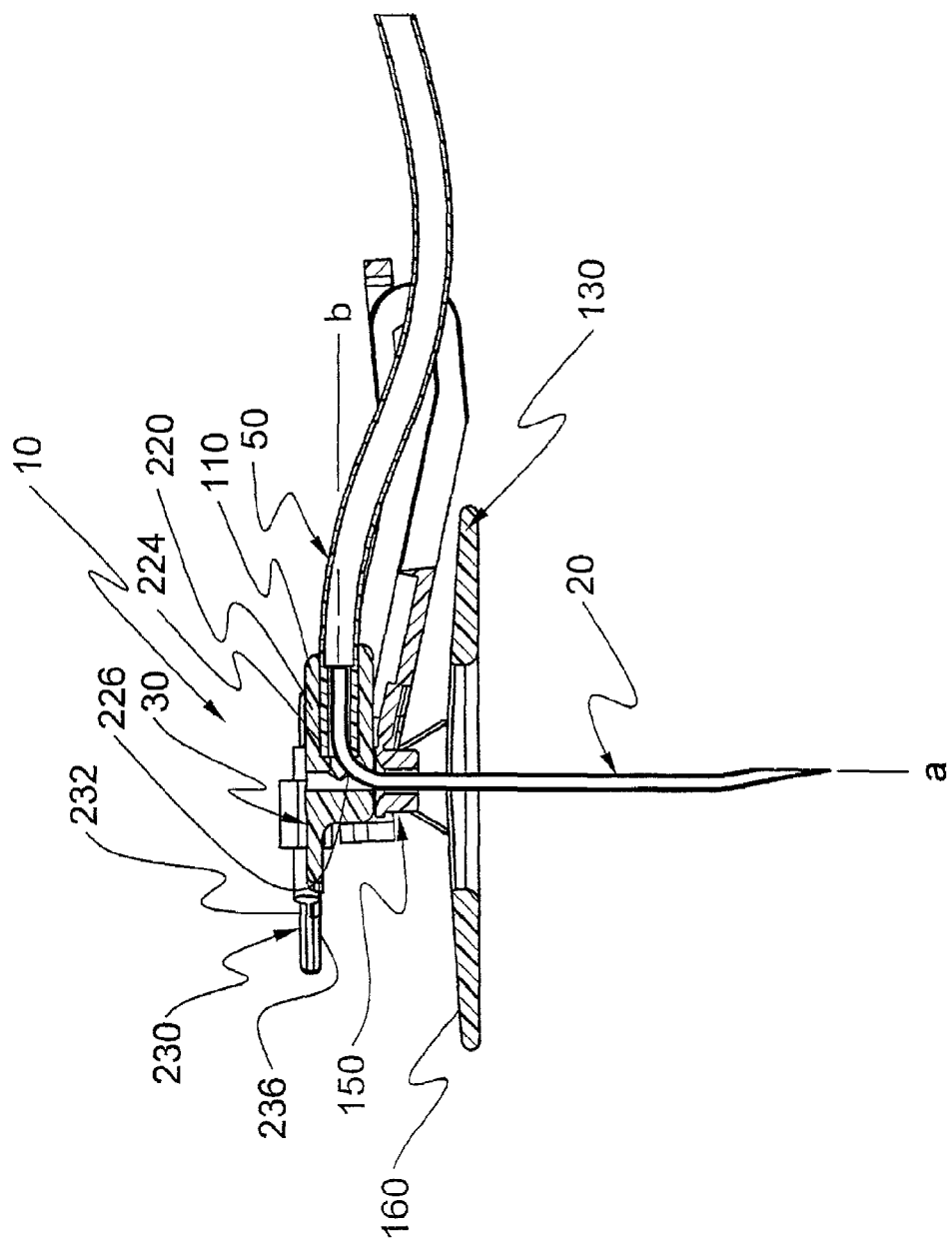
FIG. 3 is a side cross-sectional view of the safety shield apparatus shown in FIG. 1.
Figure 4:
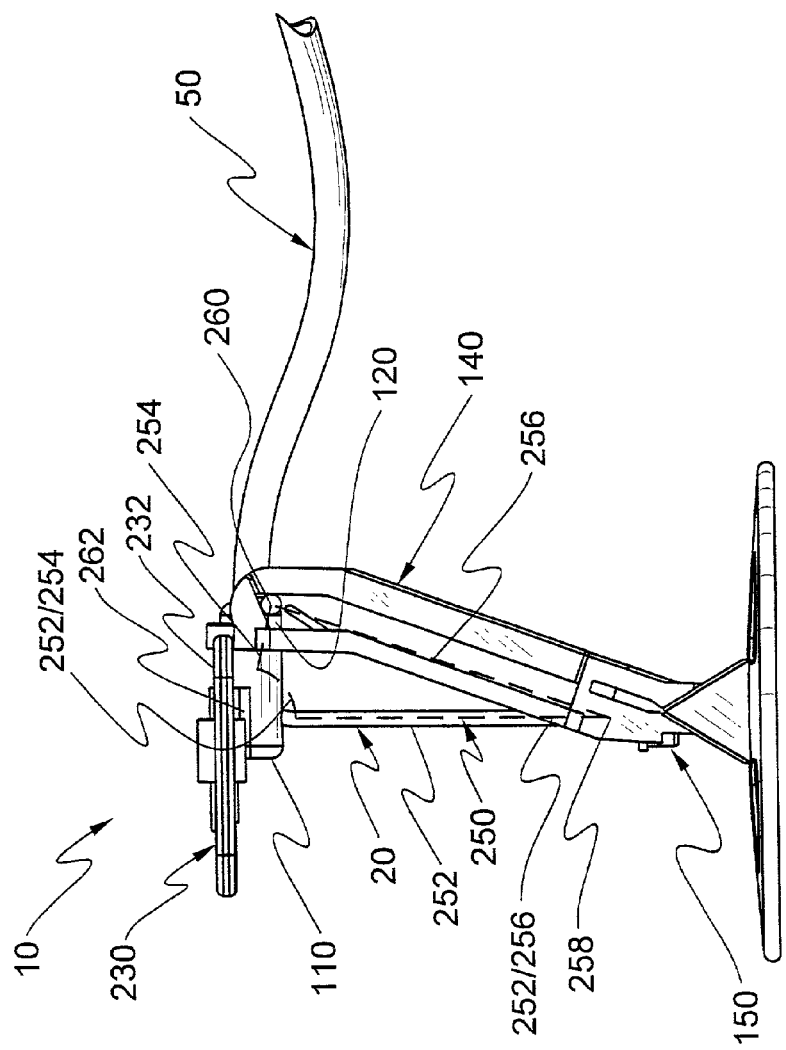
FIG. 4 is a side view of the safety shield apparatus shown in FIG. 1 in an extended position.

Turning now to the figures wherein like components are designated by like reference numerals throughout the several views. Referring initially to FIGS. 1-8, there is illustrated a safety shield apparatus 10, constructed in accordance with the principals of the present disclosure, including a needle, such as, for example, medical needle 20 having a distal portion defining a longitudinal axis a which is angularly displaced relative to a longitudinal axis b defined by a proximal portion of medical needle 20. A shield, such as, for example, shield assembly 40 is mounted with medical needle 20 and extensible, via a needle guide 150 movably guiding medical needle 20, between a retracted position (FIG. 1) and an extended position (FIG. 4). It is contemplated that needle guide 150 may be tubular. Safety shield apparatus 10 is advantageously configured to prevent hazardous exposure to a needle cannula by providing an adequate and reliable safety shield apparatus for port access needle devices which sheaths a needle upon removal from an insertion site, as will be discussed below.

Shield assembly 40 includes an elongated part 140, discussed below, and has a proximal end mounted with the proximal portion of medical needle 20 and a distal end mounted with a planar contact surface, such as, for example, stabilizer part 130, discussed below. Shield assembly 40 is extensible between the retracted position and the extended position via fixed positioning of stabilizer part 130 relative to movement of shield assembly 40. Thus, another advantage of the present disclosure is that safety shield apparatus 10 is actuated without applying substantial transverse forces to medical needle 20 during removal, resulting in a higher degree of safety to the clinician and subject. Further, this configuration of safety shield apparatus 10 advantageously provides an automatic sheathing of medical needle 20 as shield assembly 40 is manipulated to the extended position, as will be discussed.

Safety shield apparatus 10 is contemplated for use in the field of medical fluid infusion and/or collection. More particularly, safety shield apparatus 10 is envisioned to be a disposable port access needle device employing, among other things, safety features having shielding capabilities to prevent inadvertent sticking or punctures of clinicians and subjects, as well as uniform and dependable movement of sheath assembly 40 during a procedure and a locking mechanism for reliable use. The above advantages, among others, realized from the present disclosure are attained through the disclosed safety shield apparatus 10, which is extensible to a protective configuration, as discussed hereinbelow. These features of the present disclosure advantageously facilitate a safe infusion and/or collection of fluids and prevent inadvertent needle stick of a clinician and subject.

The component parts of safety shield apparatus 10 may be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate. Safety shield apparatus 10 may be integrally assembled of its constituent parts. Alternatively, portions of safety shield apparatus 10 can be monolithically formed and assembled therewith.

Figure 1:
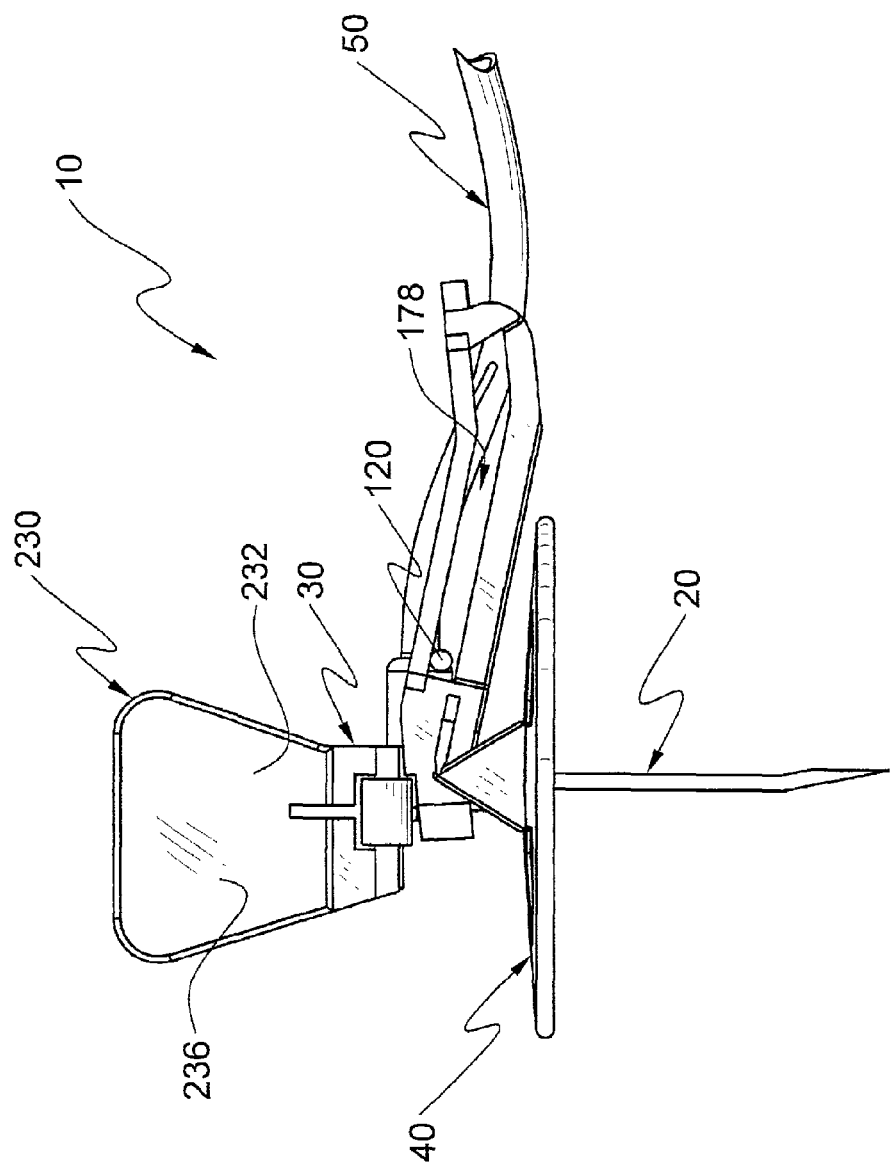
FIG. 1 is a side view of one particular embodiment of a safety shield apparatus in a retracted position, in accordance with the principles of the present disclosure.

Referring to FIG. 1, safety shield apparatus 10 is employed with a Huber type needle, such as, medical needle 20. Safety shield apparatus 10 includes a medical needle 20, a needle hub assembly 30, a shield assembly 40 and a section of medical tubing 50.

In safety shield apparatus 10, medical needle 20 is formed from an angled cannula, as shown in FIG. 7. Generally, for the purposes of providing access to medical needle 20 along a plane orthogonal to a line of percutaneous entry and parallel to a plane of an entry site, medical needle 20 is angled. This configuration is consistent with a Huber needle. Other angled medical needles may be protected by the apparatus in accordance with the present disclosure. The distal portion of medical needle 20 has an inferiorly disposed sharpened end 60. The proximal portion includes a superiorly disposed abrupt end 80 and a medially disposed bend 70 is formed therebetween.

Needle hub assembly 30, as shown in FIG. 7A, includes an appendage 100 by which needle hub assembly 30 is grasped and displaced. Needle hub assembly 30 also includes a hub body section 110, into which end 80 of medical needle 20 is securely affixed, and a slider part 120. Slider part 120 engages elongated part 140 to facilitate extension of shield assembly 140, as will be discussed below.

Figure 8:
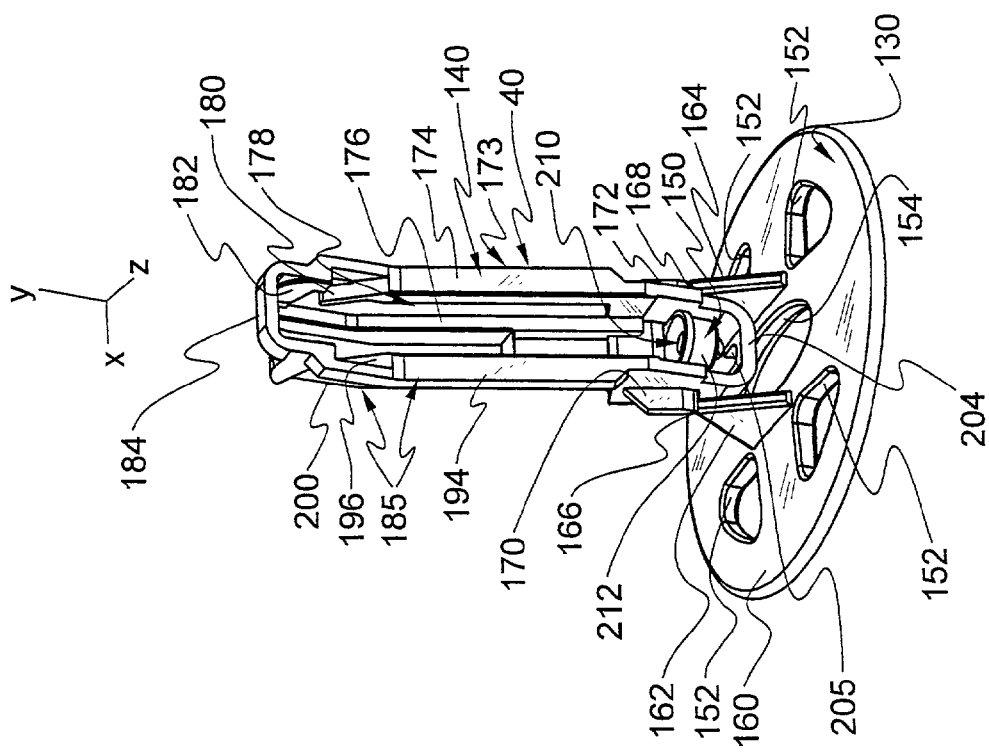
FIG. 8 is a perspective view of a shield of the safety shield apparatus shown in FIG. 1.

Referring to FIGS. 7B and 8, shield assembly 40 includes a horizontally disposed stabilizer part or finger part 130 and an elongated part 140. A needle guide 150 is disposed at a distal end of elongated part 140. Stabilizer part 130 may include a plurality of holes 152, which reduce the amount of material required to construct stabilizer part 130 and provide for line-of-sight visualization of medical needle 20, especially during needle insertion procedures and for evaporation and air circulation. A medially disposed hole 154 in stabilizer part 130 provides a through pathway for medical needle 20 and additional opportunity to see a needle insertion target. Stabilizer part 130 may be formed to have a sufficiently large accessible surface 160 to permit digital pressure to be applied in the direction of an insertion site. Such pressure is normally applied to a needle insertion site to counter anticipated frictional release forces when extracting medical needle 20 therefrom. Further, during extension of elongated part 140, pressure applied to stabilizer part 130 fixes the position of stabilizer part 130 relative to movement of elongated part 140 towards the extended position.

A pair of juxtaposed triangularly shaped struts 162 and 164, which extend outward from surface 160, may be medially disposed about hole 154. Struts 162 and 164 are configured to have a minimum top width such that a hinge connection may be made (e.g., by injection molding) with elongated part 140. Struts 162 and 164 may be hingedly connected to elongated part 140 via a pair of hinges 166 and 168, respectively. Hinges 166 and 168 are living hinges integrally molded in shield assembly 40, although elongated part 140 may be made separate from stabilizer part 130, within the scope of the disclosure and joined by other kinds of hinges, such as pin hinges, etc. Elongated part 140 may have a pair of juxtaposed outwardly extending wings 170 and 172 to which hinges 166 and 168 are respectively joined. It is contemplated that struts 162,164 may have other configurations, such as, rectangular, parabolic, etc., and of varying dimension, according to the particular requirements of a medical application and in conformity with the principles of the present disclosure.

Referring to FIGS. 7B and 8, right-side disposed members 173, of elongated part 140, may include an outwardly disposed, elongated side rail 174 and a medially disposed elongated side rail 176. Defining an axis along the length of elongated rails 174 and 176 to be a y axis of an x,y,z coordinate system, rails 174 and 176 are mutually displaced along an x axis to cooperatively form a guide channel 178. Elongated rails 174 and 176 may be mutually displaced, as shown in FIG. 8, along a z axis to provide an offset which facilitates injection mold manufacture, as one skilled in the fabrication arts.

Distally disposed relative to hinge 168, rail 174 may comprise a latching arm 180 which is angularly displaced into guide channel 178. As will be disclosed in detail hereafter, latching arm 180 may be disposed to catch slider part 120 (FIG. 7A) to function as a latch and affix medical needle 20 within a safety shield provided by shield assembly 40. Other latches are also contemplated which would so affix shield assembly 40 as a safety shield may be used within the scope of the present disclosure. Guide channel 178 may be closed distal to latching arm 180 by a joining segment 182. Segment 182 may be disposed to limit travel of slider part 120 in guide channel 178.

A bridging part 184 may be distally disposed relative to latching arm 180 and hinge 168. Bridging part 184 may be provided as a strengthening member and may not be required if other parts of shield assembly 40 are sufficiently rigid to perform as an adequate safety shield. Bridging part 184 may join right-side disposed members 173 to left-side disposed members 185 of elongated part 140, as shown in FIG. 8.

Figure 6:
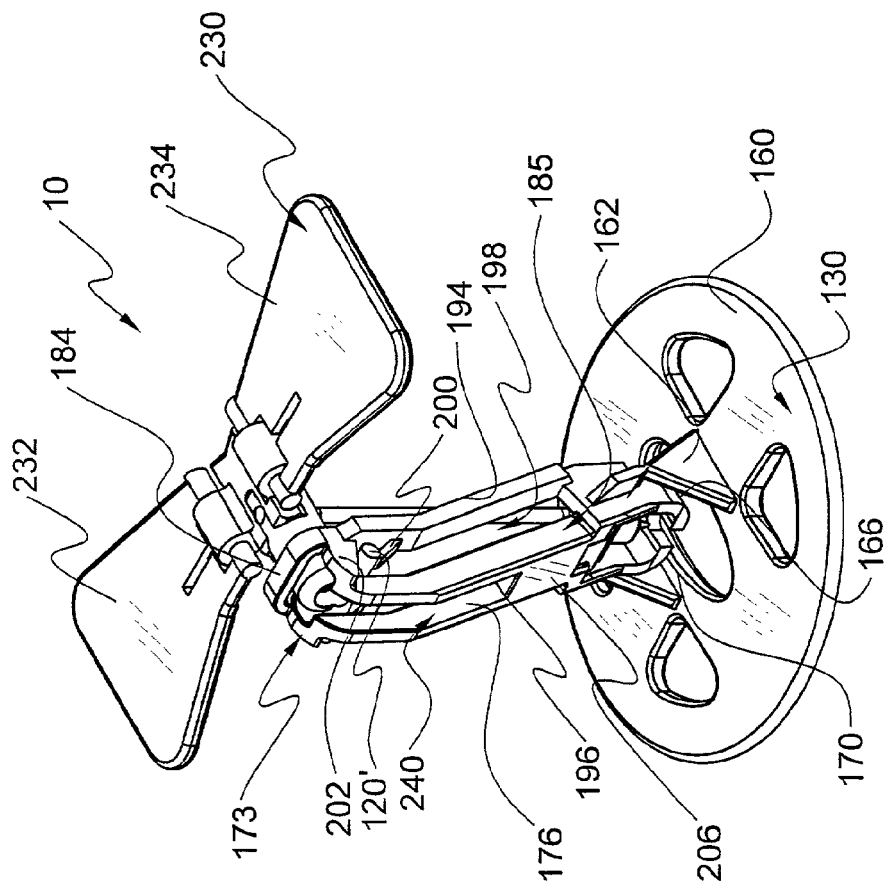
FIG. 6 is a perspective view of the safety shield apparatus shown in FIG. 1 in an extended position.

Similar to right-side disposed members 173, left-side disposed members 185 of elongated part 140 may comprise an outwardly disposed, elongated side rail 194 and a medially disposed elongated side rail 196, as shown in FIG. 6. Elongated rails 194 and 196 define the y axis and rails 194 and 196 may be mutually displaced along the x axis to cooperatively form a guide channel 198. Elongated rails 194 and 196 may be mutually displaced along the z axis to provide an offset which facilitates injection mold manufacture.

Distally disposed relative to hinge 166, rail 194 may comprise a latching arm 200 which is angularly displaced into guide channel 198. Similar to latching arm 180, latching arm 200 may be disposed to catch a slider part 120' to affix medical needle 20 within a safety shield provided by shield assembly 40. Guide channel 198 may be closed, distal to latching arm 200, by a joining segment 202. Segment 202 may be disposed to limit travel of slider part 120' in guide channel 198. This configuration facilitates affixing shield assembly 40 as a safety shield.

Bridging part 184 may be distally disposed relative to latching arm 200 and hinge 166, as discussed above. Left-side members 185 provide redundancy and, therefore, a lower likelihood of failure of a safety shield. It is contemplated that only one or a plurality of slider part/guide channel combinations be employed.

Referring to FIG. 8, a second bridging part 204, medially disposed between needle guide part 150 and hole 154 may also provide structural support for elongated part 140 between left-side and right-side members, 173 and 185, respectively. Bridging part 204 may comprise a slot 205 which is aligned with guide part 150 to permit travel of medical needle 20 therethrough. Additional structural support for elongated part 140 may be provided by an inferiorly disposed bridging part 206, as shown in FIG. 6.

Needle guide 150 may be affixed to stabilizer part 130 in line with slot 205 and hole 154, as shown in FIG. 8. Needle guide 150 may include a medially disposed through bore hole 210 and an exterior surface 212. The diameter of bore hole 210 should be large enough for facile passage of medical needle 20 therethrough, but sufficiently small to assure a firm contact between guide part 150 and medical needle 20 when elongated part 140 is vertically disposed relative to stabilizer part 130 and latched, as, by example, slider part 120 being engaged by latching arm 180. Needle guide 150 may include a tubular or cylindrical section that advantageously facilitates extension of shield assembly 140 to the extended position. The tubular or cylindrical section of needle guide 150, among other components of safety shield apparatus 10, controls motion relative to medical needle 20 during extraction from an insertion site preventing undesired "rebounding" or jerking of medical needle 20.

Referring to FIG. 7C, tubing 50 provides a communicating fluid pathway between medical needle 20 and fluid holding devices which are remote from a patient to whom medical needle 20 is affixed. As shown in FIG. 3, tubing 50 may be directly affixed to medical needle 20. Tubing 50 may be so affixed by adhesive, press fit or other ways of securing tubing to needles, which are well known in the medical device manufacturing art.

Medical needle 20 may be securely affixed to hub body section 110 which includes a bore hole 220 sized to receive tubing 50, as shown in FIG. 3. Bore hole 220 may end abruptly at a ledge 224 which surrounds a smaller hole defined by a constraining rim 226. In this way, securely affixing medical needle 20 into tubing 50 which resides in bore hole 220, assures rigid containment of both tubing 50 and medical needle 20 within body section 110. Tubing 50 may be securely attached to body section 110 within bore hole 220 by adhesive, insert molding, press fit, etc.

Appendage 100 includes a digital (manipulable) interface which may be facilely gripped by a clinicians fingers. Appendage 100 may have a winged interface 230, as shown in FIGS. 1-5. Winged interface 230 may include two winged parts, 232 and 234. Winged parts 232 and 234 may be hinged or flexible and horizontally disposed, as shown in FIGS. 2 and 3 to provide a low silhouette until safety shield apparatus 10 is to be removed from an insertion site. This configuration advantageously permits less obstruction for tape down and other site preparation over extended periods of use.

As shown in FIG. 1, winged part 232 (and winged part 234) may be articulated to a more vertical orientation when extracting medical needle 20. Winged interface 230 permits extraction forces to be applied directly above and in-line with a longitudinal axis insertion line of medical needle 20. To aid in gripping and transferring extraction forces to winged interface 230, winged parts 232, 234 may include corrugation, texturing or other process to increase surface friction.

The manufacture of safety shield apparatus 10 parts may be accomplished by injection is molding of hub assembly 30 and shield assembly 40, both of which may be injection molded using synthetic resinous material, such as polypropylene. Medical tubing 50 may be selected from medical tubing currently commercially available. To assemble safety shield apparatus 10, slider parts may be displaced into slideable containment in an associated guide channel, such as slider part 120 being displaced into guide channel 178. In FIG. 6, a tubing channel 240 may be formed by separation of juxtaposed rails 176 and 196. Tubing 50 may be displaced through channel 240 and into bore hole 50, as previously disclosed. End 80 of medical needle 20 is displaced into tubing 50 and securely affixed thereat.

As seen in FIGS. 1-3, safety shield apparatus 10 may be properly sterilized and otherwise prepared for storage, shipment and use. Safety shield apparatus 10 may be properly affixed, via stabilizer part 130, and inserted with a subject (not shown) for a port access medical procedure, such as, for example, one or a plurality of infusion and/or collection of fluid procedures. Upon completion of the medical procedure (s), force may be applied to surface 160 of stabilizer part (finger pad) 130 while retracting forces are applied to winged parts 232 and 234. Thus, stabilizer part 130 remains in a fixed position, relative to movement of shield assembly 40 to the extended position. Needle guide 150 may slidably support medical needle 20 to facilitate extension of shield assembly 40 and prevent undesired "rebound" or jerking motion during extraction.

Figure 5:
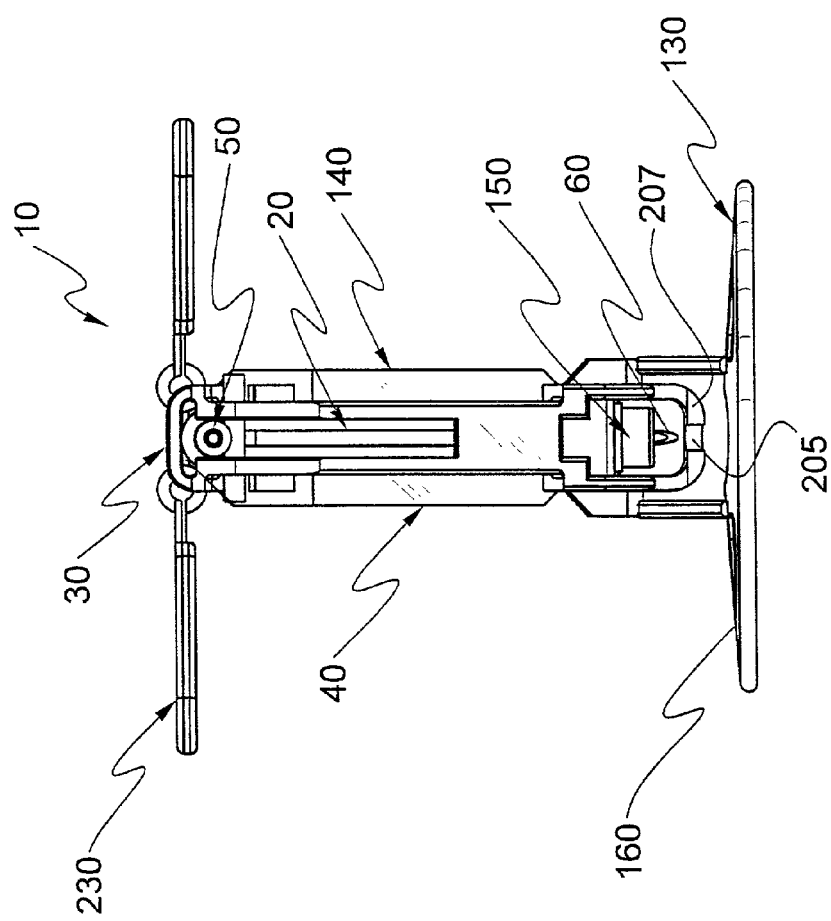
FIG. 5 is a front view of the safety shield apparatus shown in FIG. 1 in an extended position.

Medical needle 20 is thereby extracted from an insertion site. As medical needle 20 is extracted, hub assembly 30 is displaced away from surface 160 displacing slider parts 120 and 120' along respective guide channels 178 and 198. Elongated part 140 is thereby articulated until sharpened tip 60 of medical needle 20 is displaced into protective shielding of shield assembly 40 and slider parts 120 and 120' are unreleasably, respectively engaged by latching arms 180 and 200. As shown in FIGS. 4A and 5, sharpened tip 60 of medical needle 20 is fully enclosed by shield assembly 140.

To assure shielding of sharpened tip 60, medical needle 20 may be captured and held within a rigid, triangular frame formed having sides made of portions of medical needle 20, hub body section 110, elongated part 140 and guide part 150. As shown in FIG. 4, a triangle 250 is formed by dashed lines which represent legs 252, 254 and 256 of triangle 250. For clarity, each internal angle of triangle 250 is referenced as an angle between adjacent legs (e.g., the angle associated with bend 70 of medical needle 20 and slider part 120 is referenced by angle 252/254.)

In an alternate embodiment, when elongated part 140 is articulated away from stabilizer part 130 and slider parts 120 and 120' are respectively affixed by latching arms 180 and 200 (FIG. 5), elongated part 140 firmly engages exterior surface 212 of guide part 150 (FIG. 4A). As medical needle 20 is restrained within bore hole 210, an endpoint 258 of each leg 252 and 256 and angle 252/256 is defined (FIG. 4). An angle 252/254 is defined by construction of needle bend 70 and hub body section 110. All internal angles of triangle 250 are predetermined. With all internal angles known, and at least one side determined, the size and structure of triangle 150 is fixed. A common endpoint 260 for legs 256 and 254 is defined to be at slider part 120. A common endpoint 262 for legs 252 and 254 is at bend 70. Thus, an attempt to force hub assembly 30 toward stabilizer part 130 and thereby to drive sharpened end 60 outwardly through hole 154 is defeated, and medical needle 20 is safely contained within shield assembly 40.

Figure 34:
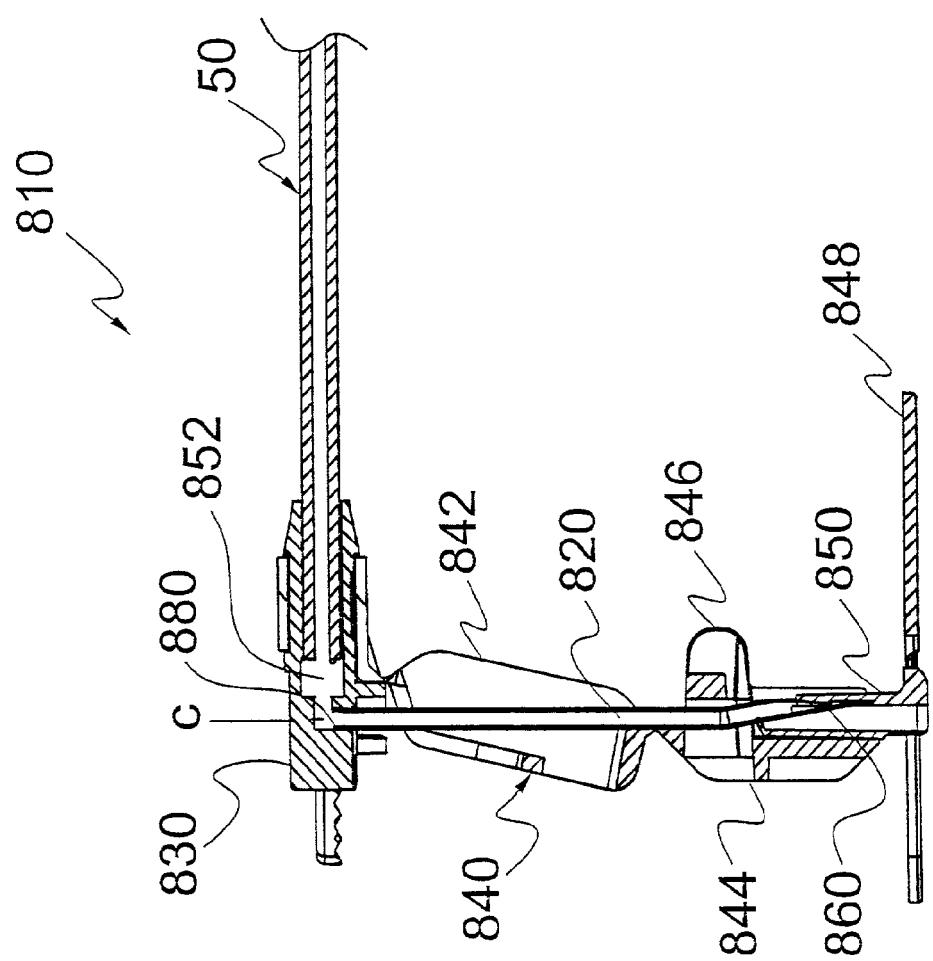
FIG. 34 is a side cross-sectional view of an alternate embodiment of a needle and hub.

Within the scope of the present disclosure, a straight medical needle may be used in place of medical needle 20, see for example, the embodiment shown in FIG. 34 and discussed hereafter. In such a case, a hub assembly which is firmly and securely affixed to the straight needle and which permits fluid communication with medical tubing would have a slider part (similar to slider part 120) transversely displaced relative to the straight medical needle to engage a guide channel (similar to guide channel 178).

Figure 9:
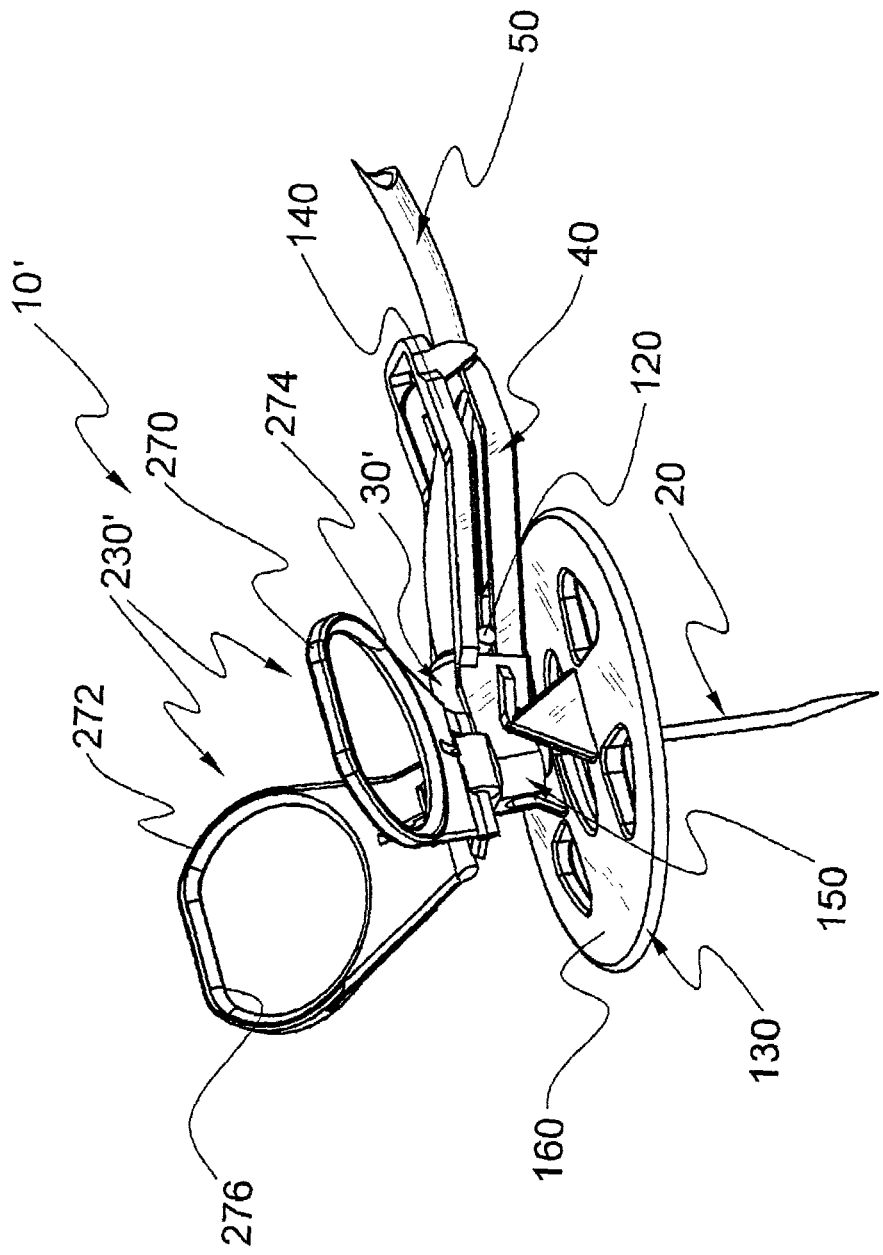
FIG. 9 is a perspective view of another embodiment of the safety shield apparatus.
Figure 10:
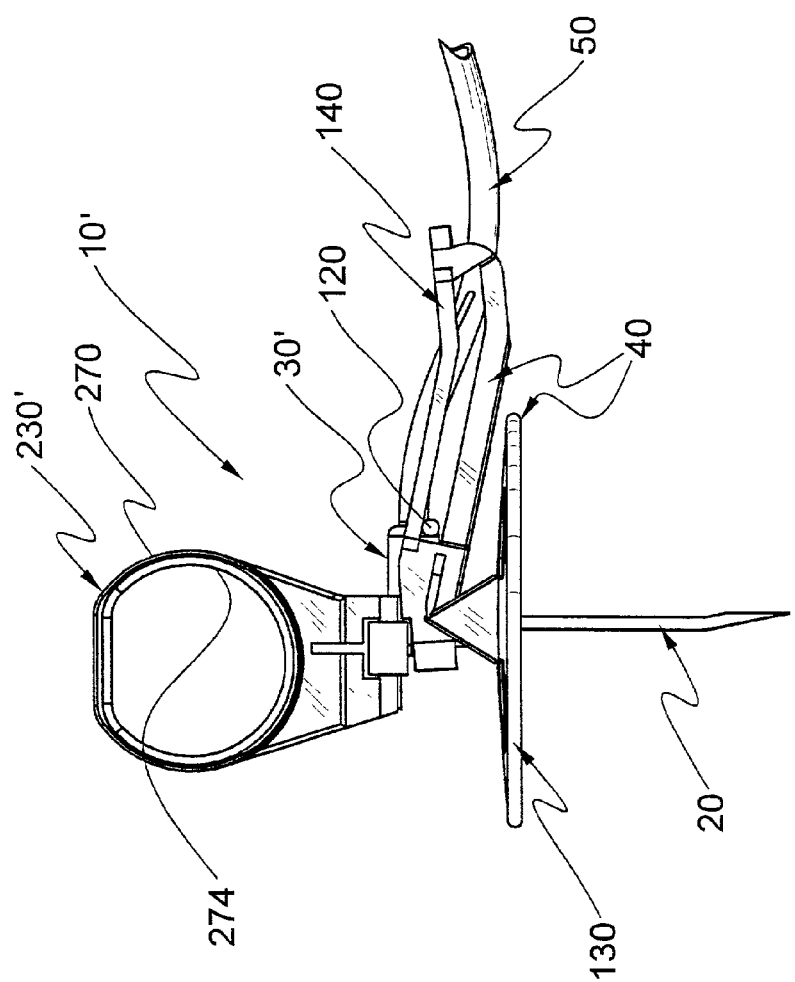
FIG. 10 is a side view of the safety shield apparatus shown in FIG. 9.

Referring to FIGS. 9 and 10, another embodiment of a safety shield apparatus 10', similar to the apparatus and methods of use of safety shield apparatus 10 described above, is shown. Safety shield apparatus 10' may have a winged interface 230' used to apply extractive force to pull medical needle 20 of safety shield apparatus 10' from an insertion site. As shown in FIG. 9, safety shield apparatus 10' has a pair of wings 270 and 272 affixed to a hub assembly 30'. Winged interface 230' may have holes disposed in wings 270 and 272 to form pull rings 274 and 276, respectively. Such rings are provided to facilitate applying pull force in direct line with medical needle 20 when winged interface 230' is upwardly disposed as shown in FIG. 10.

Figure 11:
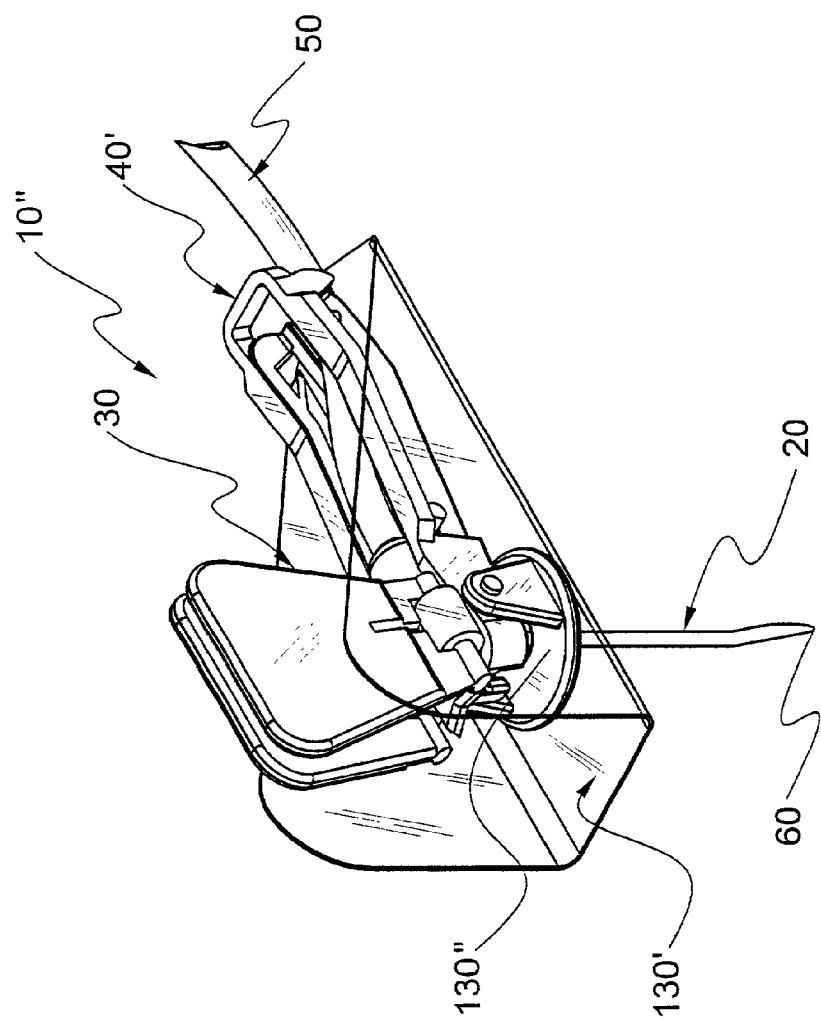
FIG. 11 is a perspective view of an alternate embodiment of the safety shield apparatus, in a retracted position.
Figure 12:
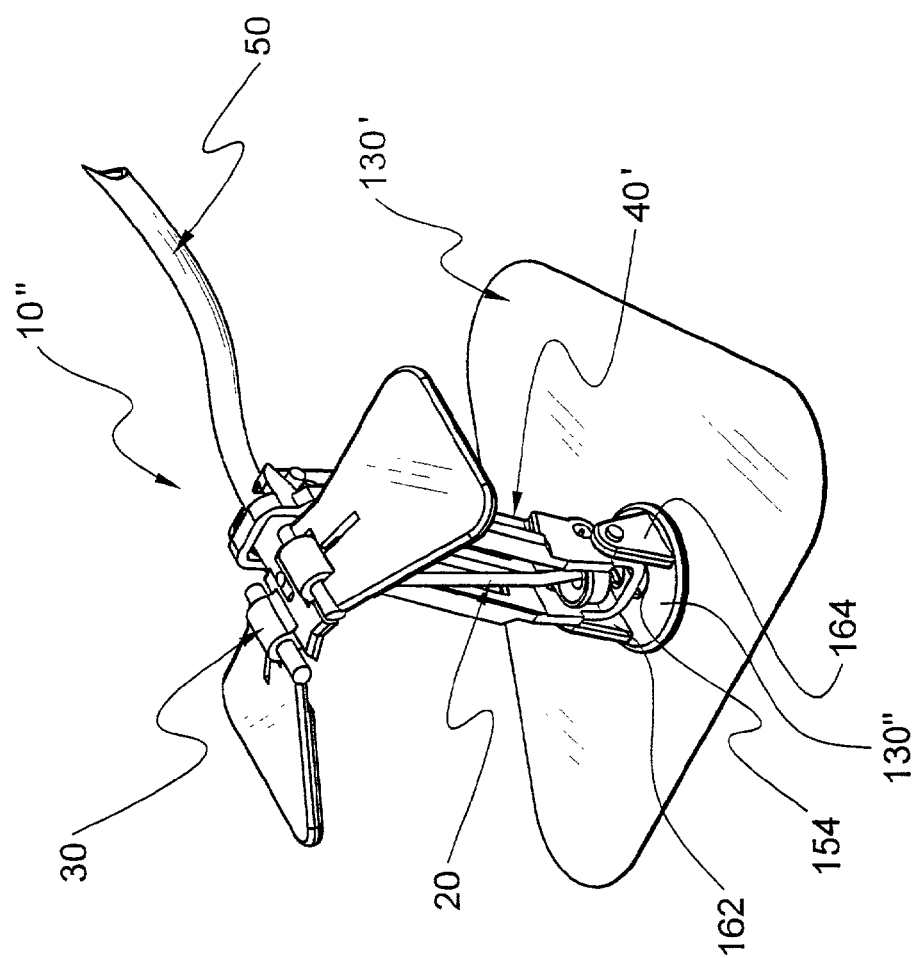
FIG. 12 is a perspective view of the safety shield apparatus shown in FIG. 11, in an extended position.

Referring to FIGS. 11 and 12, another embodiment of a safety shield apparatus 10'', similar to the apparatus and methods of use of safety shield apparatus 10 described above, is shown. Safety shield apparatus 10'' includes a medical needle 20, a needle hub assembly 30, a shield assembly 40' and a section of medical tubing 50.

As shown in FIG. 11, safety shield apparatus 10'' may have a stabilizer part or finger pad 130', which may be made from a transparent material, although translucent or opaque material may be used within the scope of the present disclosure. Further, stabilizer part 130' may also be flexible allowing it to be folded about other parts of safety shield apparatus 10'' during medical needle 20 insertion. Stabilizer part 130' may be a thin sheet having sufficient tensile strength to allow shield assembly 40' to be displaced to sheath and protect medical needle 20 without tearing, similar to stabilizer part 130, discussed above. One advantage of configuring stabilizer part 130' as a thin sheet is to permit tactile feedback about the insertion site, while withdrawing medical needle 20. In a Huber needle application, medical needle 20 penetrates a septum of an implanted port, tactile feedback and stabilization of the port itself during medical needle 20 extraction is desirable.

In FIG. 11, stabilizer part 130' may be folded about safety shield apparatus 10'' to permit visual access to medical needle 20. In FIG. 12, stabilizer part 130' may be broadly spread to permit manual access and application of force while extracting medical needle 20 to be captured within the shield provided by shield assembly 40'.

Stabilizer part 130' may include an anchor part 130'' both having a centrally disposed hole 154 for passage of medical needle 20. Anchor part 130'' may have a sufficient diameter to provide a base for struts 162 and 164 and a secure attachment to stabilizer part 130'. Stabilizer part 130' may be mechanically affixed, injection molded, adhered, etc., to anchor part 130''. Stabilizer part 130' may be fabricated from materials such as polyolefin, polyurethane film, woven or non-woven fabrics, synthetic foam, etc.

Figure 13:
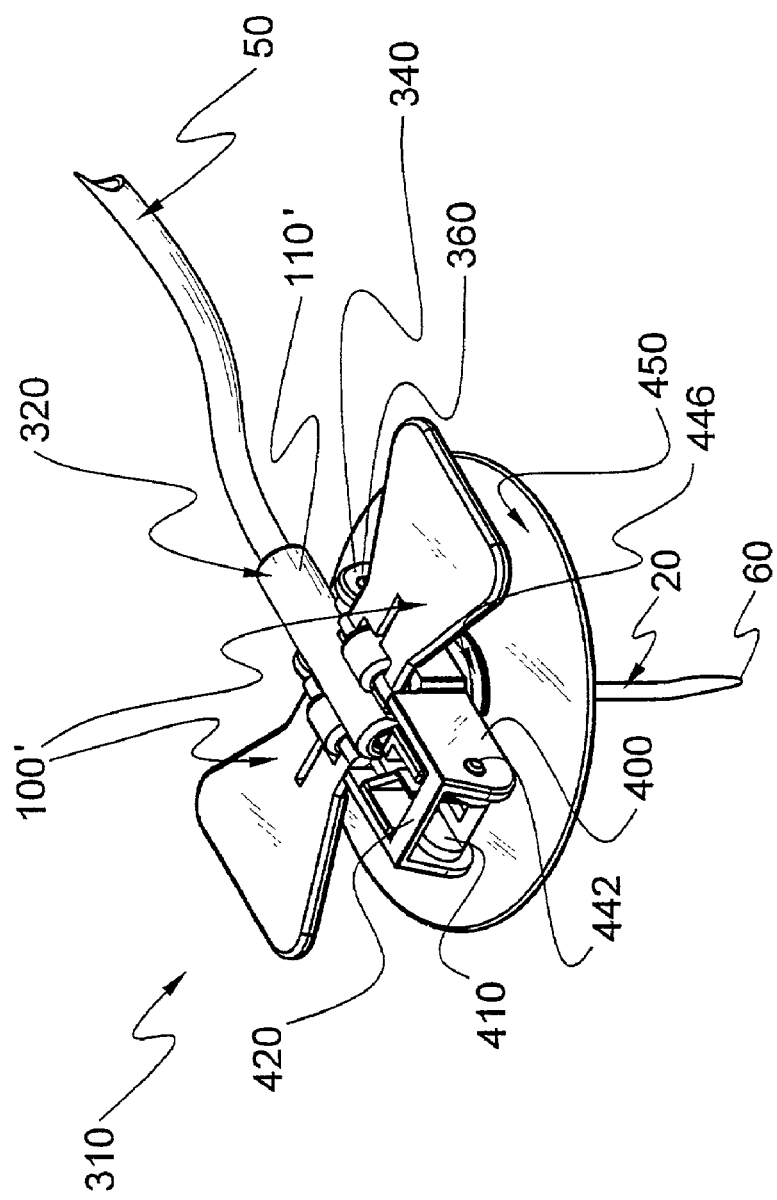
FIG. 13 is a perspective view of another alternate embodiment of the safety shield apparatus in a retracted position.

Referring to FIGS. 13-19, another embodiment in accordance with the present disclosure is shown. As shown in FIG. 13, a safety shield apparatus 310, similar to the apparatus and methods of use of safety shield apparatus 10 described above, includes a medical needle 20, a needle hub assembly 330, a shield assembly 340 and a section of medical tubing 50.

A needle hub assembly 330, may include an appendage 100' by which hub assembly 330 can be grasped and displaced, and a hub body section 110' into which end 80 of medical needle 20 is securely affixed. Hub assembly 330 may include a pin hinge 360 whereby hub assembly 330 is hingeably affixed to shield assembly 340. Living hinges are also contemplated.

Figure 17:
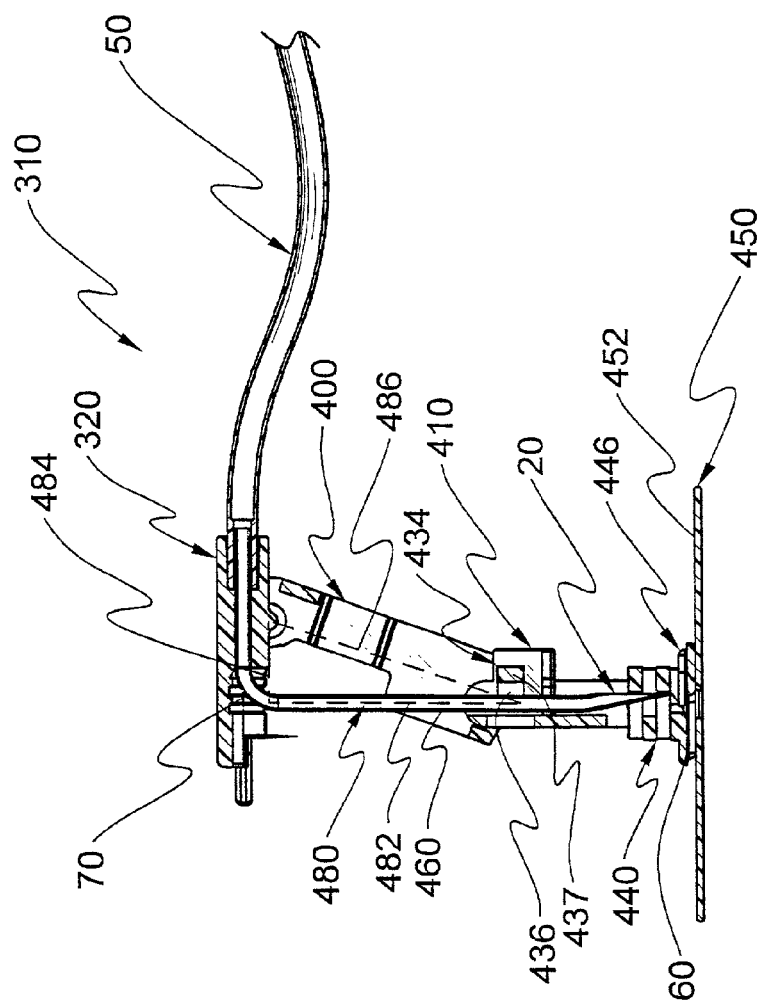
FIG. 17 is a side cross-sectional view of the safety shield apparatus shown in FIG. 15.
Figure 18:
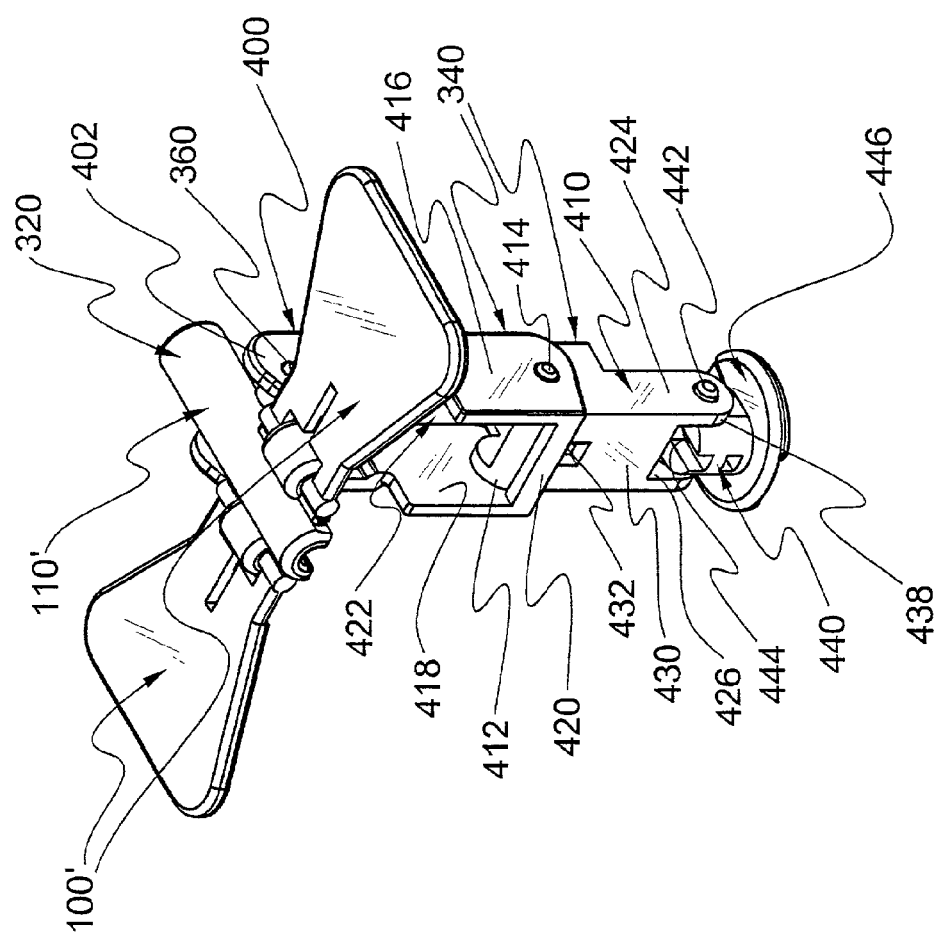
FIG. 18 is a perspective view of the component parts of the safety shield apparatus shown in FIG. 13.

Referring to FIGS. 17 and 18, shield assembly 340 may include a first articulating part 400 having an end 402 which is joined to hub assembly 320 via pin hinge 360. Articulating part 400 may be hingeably associated with a second articulating part 410, at a first end 412 through a pin hinge 414. Living hinges are also contemplated.

Articulating part 400 may be symmetrical about a longitudinal axis having a pair of side parts 416 and 418, as shown in FIG. 18. Articulating part 400 may also be single sided. A bridging member 420 may join and support separation of side part 416 and 418 and thereby defines a rectangular space 422 between parts 416 and 418.

Figure 15:
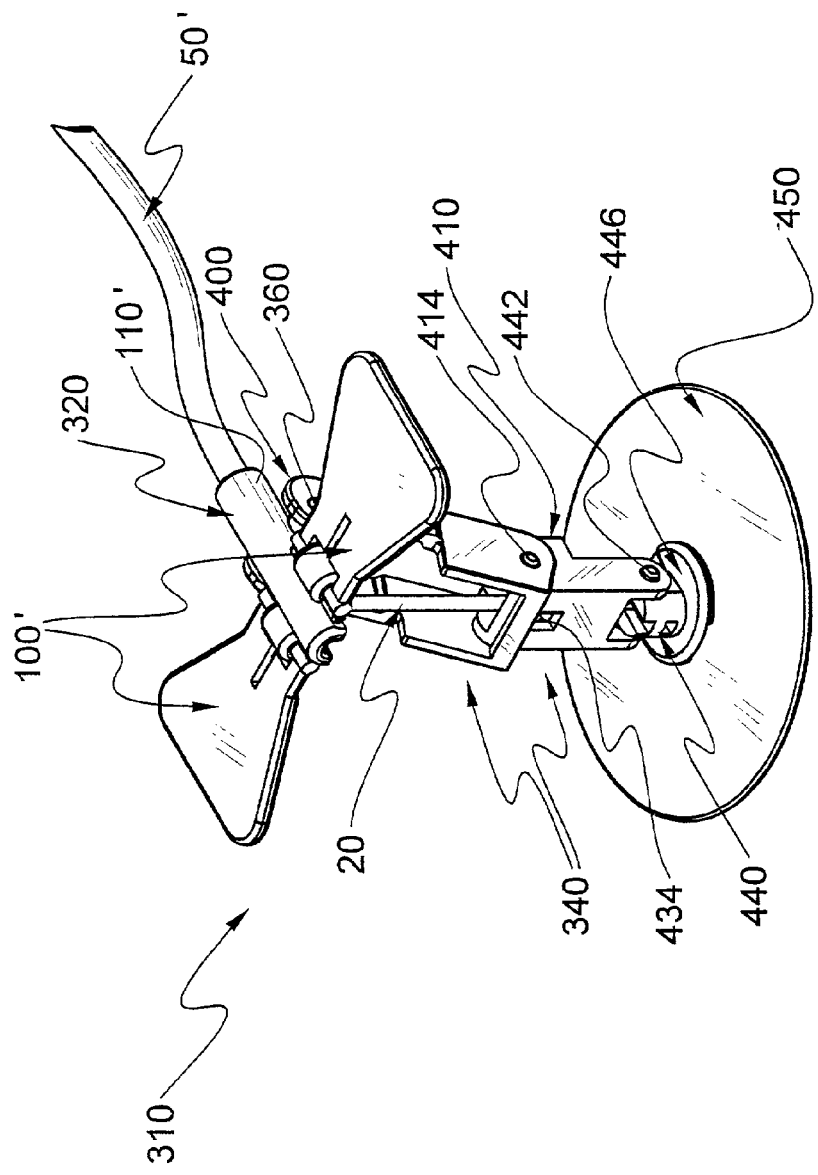
FIG. 15 is a perspective view of the safety shield apparatus shown in FIG. 13, in an extended position.
Figure 16:
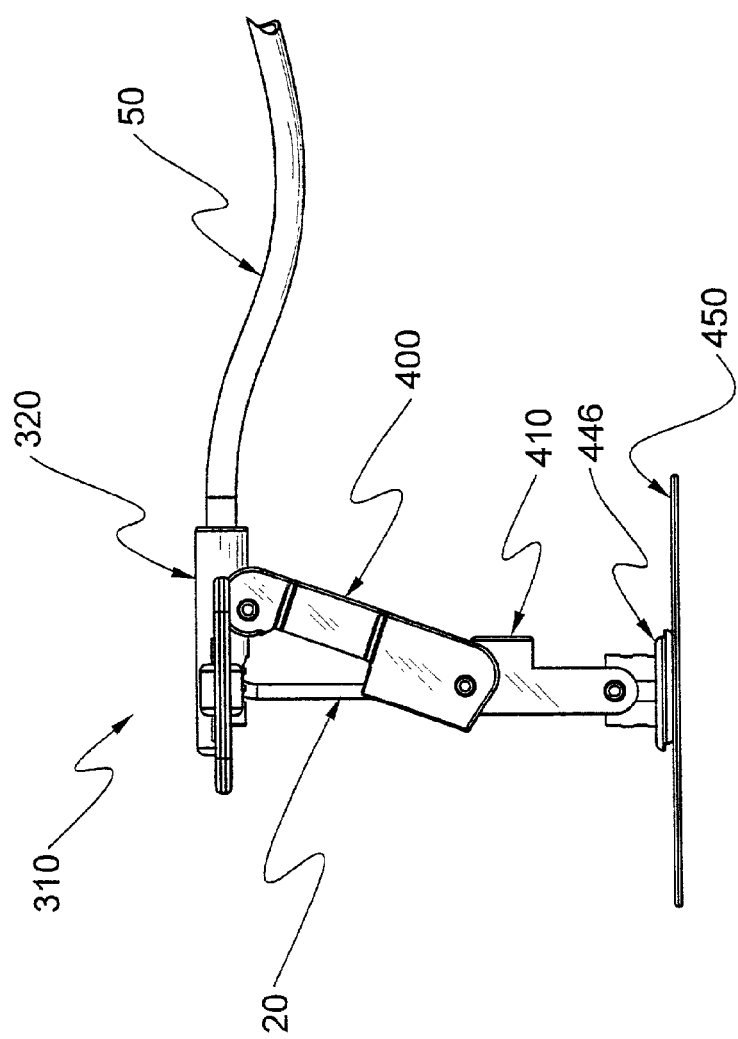
FIG. 16 is a side view of the safety shield apparatus shown in FIG. 15.

Articulating part 410 may be shorter than part 400 and includes side members 424 and 426, as seen in FIG. 18. Parts 400,410 may be of varying relative dimension. A bridging member 430 joins and supports separation of side parts 424 and 426. Side parts 424 and 426 are separated such that articulating part 410 may be foldably disposed within space 422, permitting shield 340 to be compacted into a low silhouette, as shown in FIG. 13. Disposed in articulating part 410, between bridging member 430 and bridging member 420 of articulating part 400, may be an opening 432. Opening 432 permits a clip 434 to be molded into articulating part 410, as shown in FIG. 17. Clip 434 may have a stem section 436 coupled to a latch 437 which is displaced beyond medical needle 20 when shield assembly 340 is extended, as shown in FIGS. 15-17. Latch 437 catches medical needle 20 to affix shield assembly 340 in a protective position about medical needle 20 and sharpened tip 60, as disclosed in detail hereafter. Other clips may be used within the scope of the present disclosure.

At a second end 438, part 410 may be hingeably affixed to a linear guide 440. Linear guide 440 may include a medially disposed through hole 444 which is slidably disposed about medical needle 20 (FIGS. 14 and 17) and acts as a guide for shield assembly 340 as articulating parts 400 and 410 are unfolded to provide a protective sheath for medical needle 20 and sharpened tip 60. As shown in FIG. 18, distal from hinge 442, linear guide 440 may include a flattened plate 446, similar to stabilizer part 130, discussed above.

A thin resilient disk 450 may include an accessible surface 452 and, thereby, provides for tactilely sensing disposition of a target implant and for distributing tactile forces across a broader surface area than that which is accessible through finger contact alone. By making disk 450 of transparent or material through which medical needle 20 may be seen, an insertion site may be more easily viewed during a percutaneous entry procedure. Also, a resilient disk 450 may be folded about hub assembly 320 to provide an unobstructed view during the entry procedure.

As one who is skilled in injection mold manufacture and parts molding understands, hub assembly 320 and shield assembly 340 may be molded from a single injection molded part, as such may be preferred to reduce the cost of manufacture of safety shield apparatus 310. Medical grade polypropylene may be used to mold assemblies 320 and 340. Assemblies 320 and 340 are generally symmetrical about an axial midline defined by a shaft 460 of medical needle 20 (FIG. 14).

Figure 14:
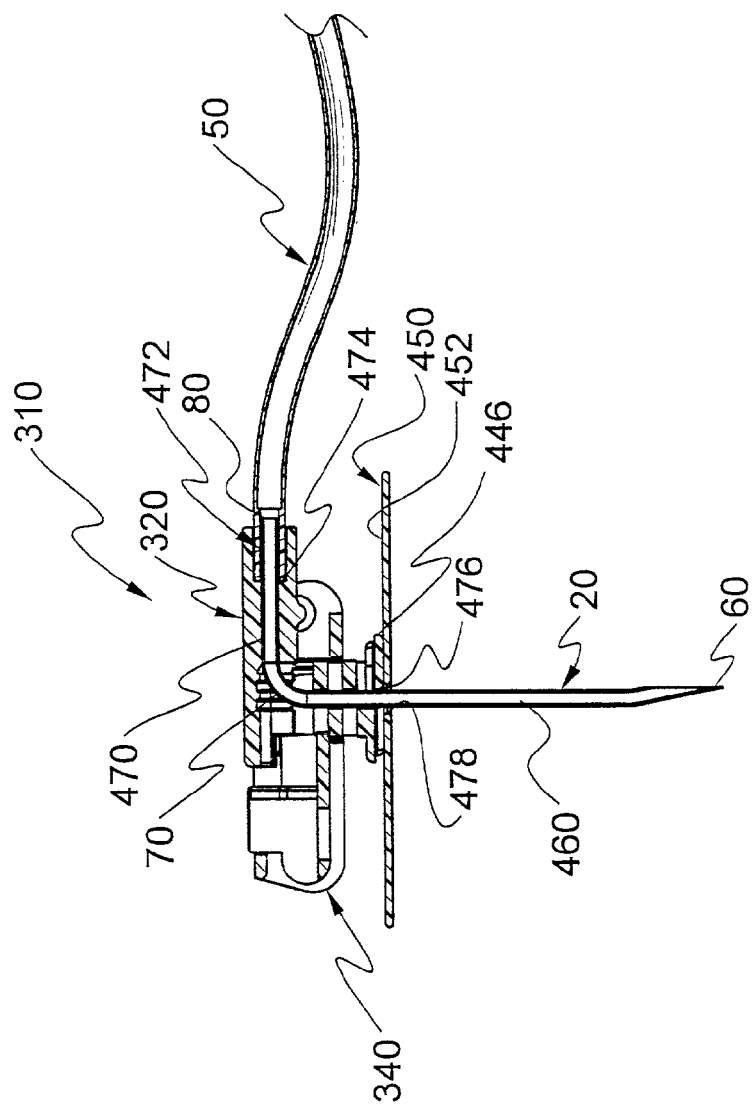
FIG. 14 is a side cross-sectional view of the safety shield apparatus shown in FIG. 13.

As shown in FIG. 14, hub assembly 320 may comprise a through hole 470 which is narrowed toward disposition of bend 70 of medical needle 20 and is enlarged toward an attachment site 472 between medical needle 20 and tubing 50. An abrupt edge 474 retards the length of insertion of tubing 50 such that when tubing 50 is adhesively affixed to medical needle 20 about end 80, a combination of such adhesion and bend 70 securely affixes medical needle 20 in needle hub assembly 320. Other needle to tubing joints are possible within the scope of the present disclosure. With shield assembly 340 hingeably affixed to hub assembly 320 as shown in FIG. 18, safety shield apparatus 310 may be assembled by displacing medical needle 20 through space 422 in articulating part 400, through hole 444 in guide 440 of articulating part 410 and through a pair of medially disposed holes 476 and 478 of plate 446 and disk 450, respectively, as shown in FIG. 14.

In an alternate embodiment, to assure shielding of sharpened tip 60, medical needle 20 may be captured and held within a rigid structure, a triangular frame is formed having sides made up of portions of medical needle 20, hub body section 110', articulating part 400 and that portion of articulating part 410 which includes latching structure associated with clip 434. As shown in FIG. 17, a triangle 480 is formed by dashed lines which represent legs 482, 484 and 486 of triangle 480. Leg 484 is defined by end points at bend 70 and pin hinge 360. Leg 486 is disposed parallel to radius of angle of rotation of articulating part 400 and is defined by an end point at pin hinge 360 and intersection with shaft 460 of needle 20. Leg 482 is defined by an end point at bend 70 and point of intersection with line 486. For clarity, each internal angle of triangle 480 is referenced as an included angle between adjacent legs (e.g., the internal angle at bend 70 between shaft 460 of medical needle 20 and leg 484 toward pin hinge 360 is referenced by angle 482/484).

When shield assembly 340 is unfolded and part 400 is articulated away from stabilizer parts (plate 446 and disk 450) and part 410 is rotated into alignment with shaft 460 as shown in FIGS. 15-17, clip 434 catches and affixes part 410 relative to needle 20. So affixed, triangle 480 is defined. Thus, triangle 480 establishes a rigid structure assuring protective cover for needle 20 and tip 60 which is then protected by shaft 460 surrounding guide 440. Angle 482/484 is fixed by structure associated with bend 70 and pin hinge 360. Angle 484/486 is determined by clip 434 being disposed to latch shaft 460. Angle 482/486 is defined because the other two angles of triangle 480 are so defined. Thus, an attempt to force hub assembly 320 toward stabilizer parts 446 and 450 and thereby to drive sharpened end 60 outwardly through holes 476 and 478 is defeated, and medical needle 20 is safely contained within shield assembly 340. Shield assembly 340 may be constructed such that angle 482/486 is zero when clip 434 is affixed to shaft 460.

Referring to FIGS. 19-30, an embodiment of a safety shield apparatus 744 is shown including a port access needle 746 including a shield 750 of hingedly connected segments 612' and 614' for protecting distal end 747 of needle 746 after use in a medical procedure. Needle 746 may be oriented in two axes such that a distal needle portion 746A is oriented at an axis 90 degrees relative to an axis defined by a proximal needle portion 746B. It is contemplated that distal needle portion 746A and proximal needle portion 746B may be oriented at various angular displacements. As shown in FIGS.

19-29, segments 612' and 614' may be configured for a low profile such that the segments may be folded into each other in a pre-use state as a result of either segment having smaller dimensions than the other.

Figure 19:
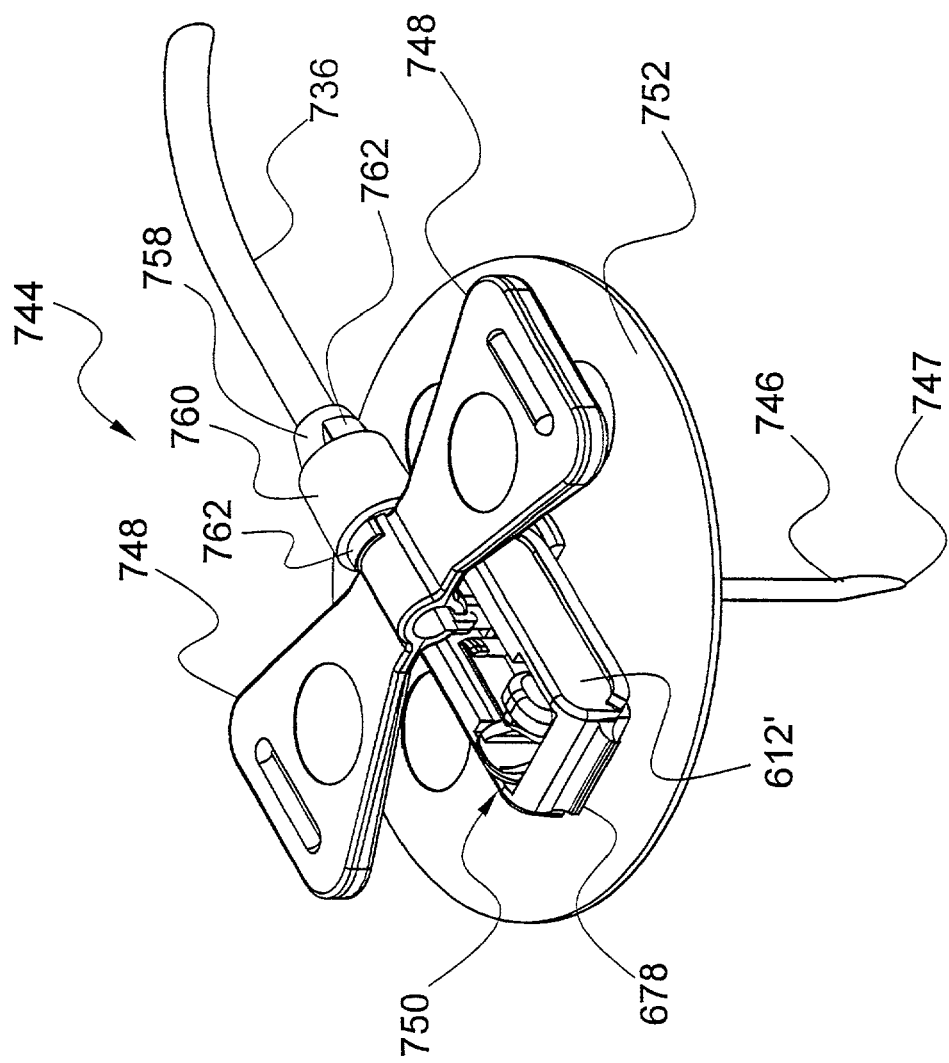
FIG. 19 is a perspective view of another alternate embodiment of the safety shield apparatus in a retracted position.
Figure 20:
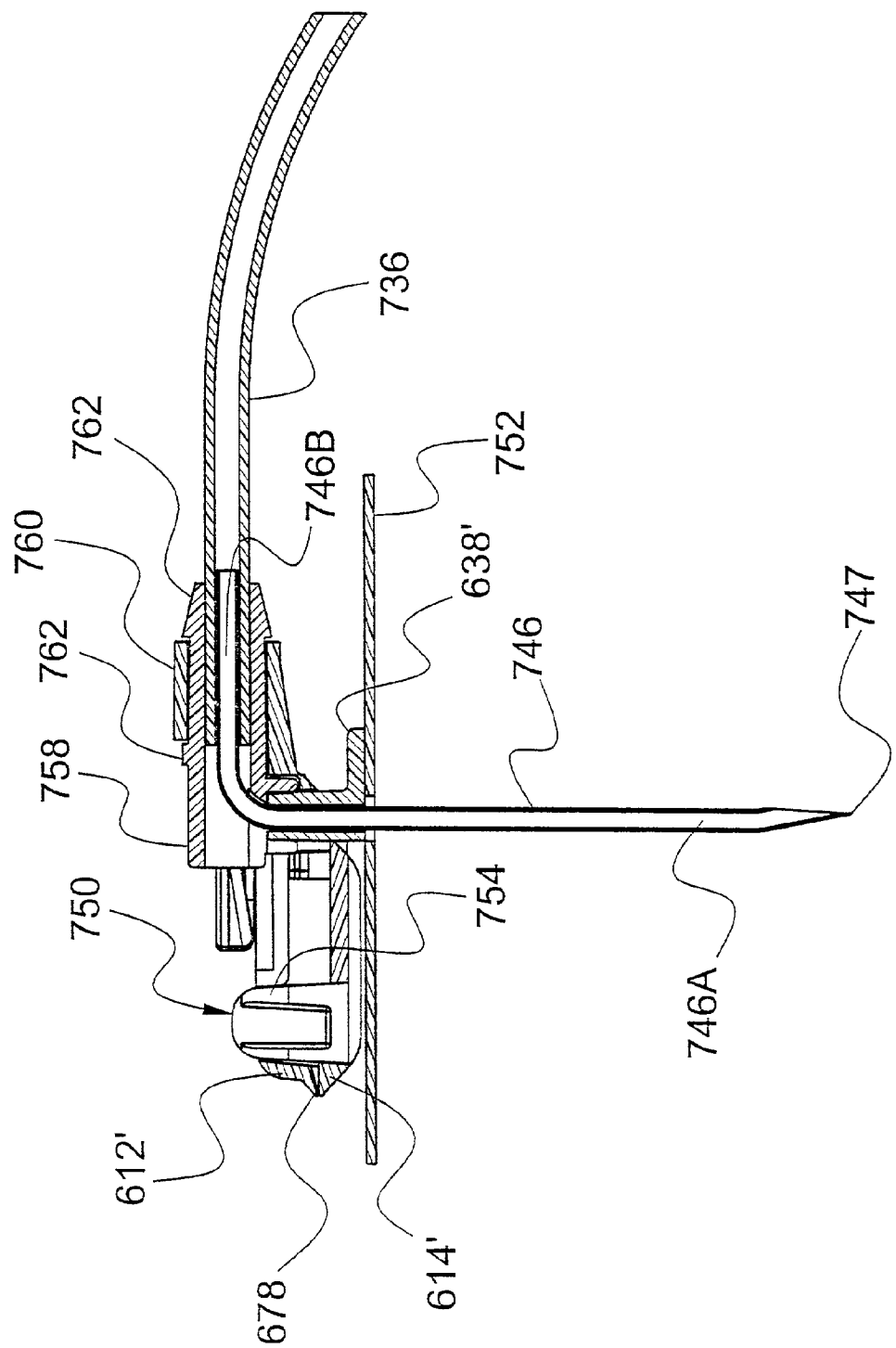
FIG. 20 is a cross-sectional view of the safety shield apparatus shown in FIG. 19.
Figure 21:
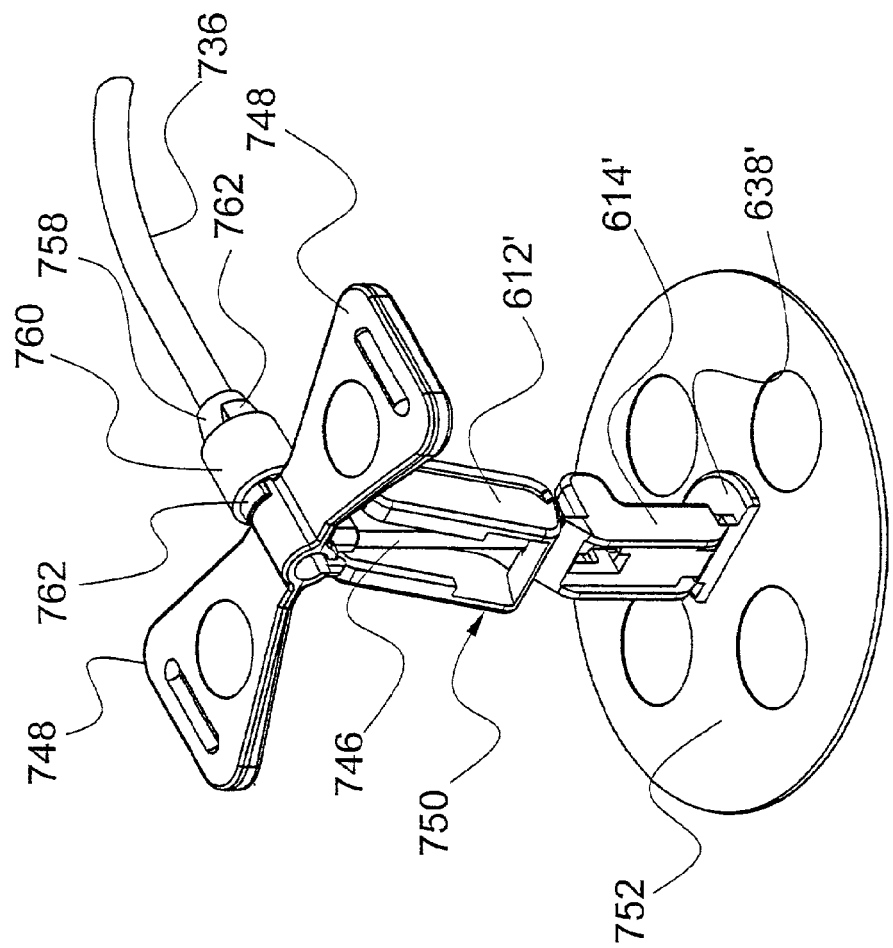
FIG. 21 is a perspective view of the safety shield apparatus shown in FIG. 19 fully extended.
Figure 22:
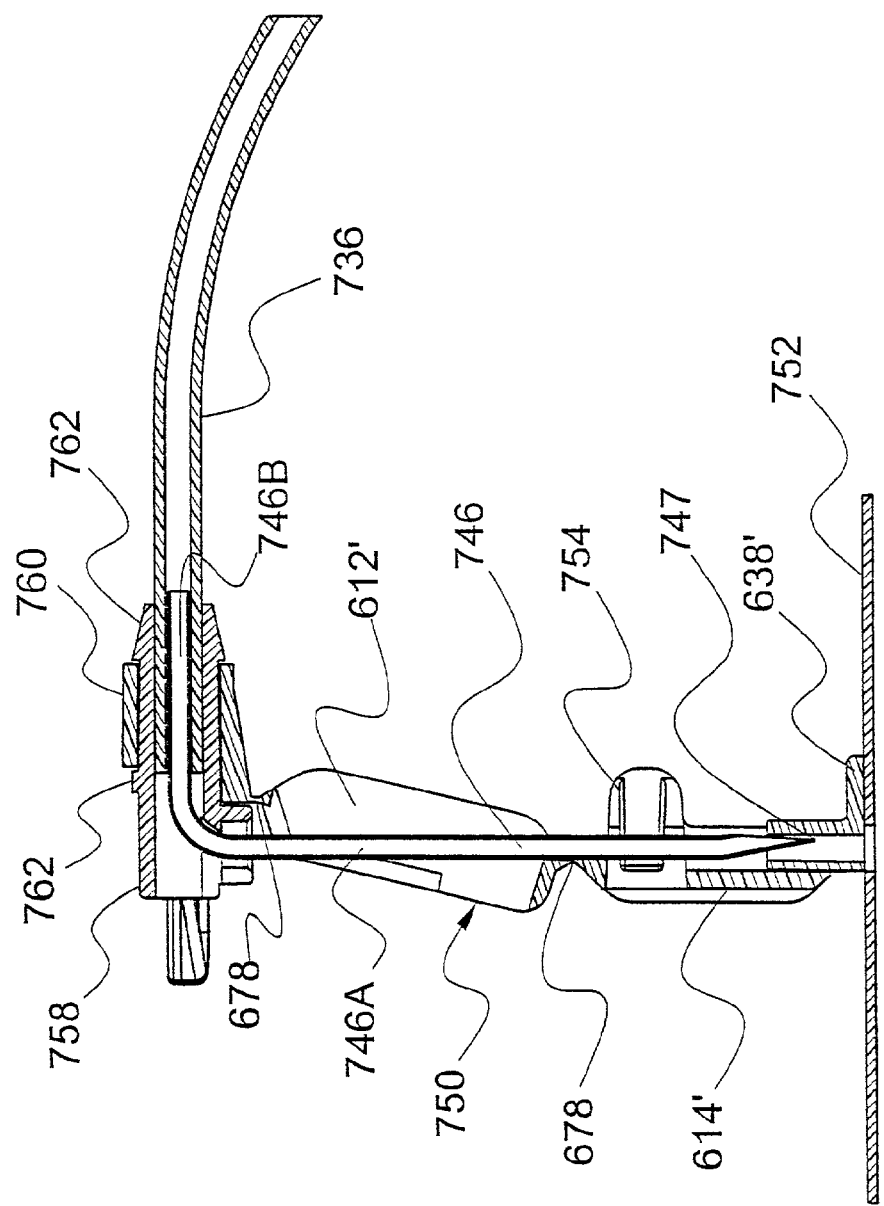
FIG. 22 is a cross-sectional view of the safety shield apparatus shown in FIG. 21.
Figure 26:
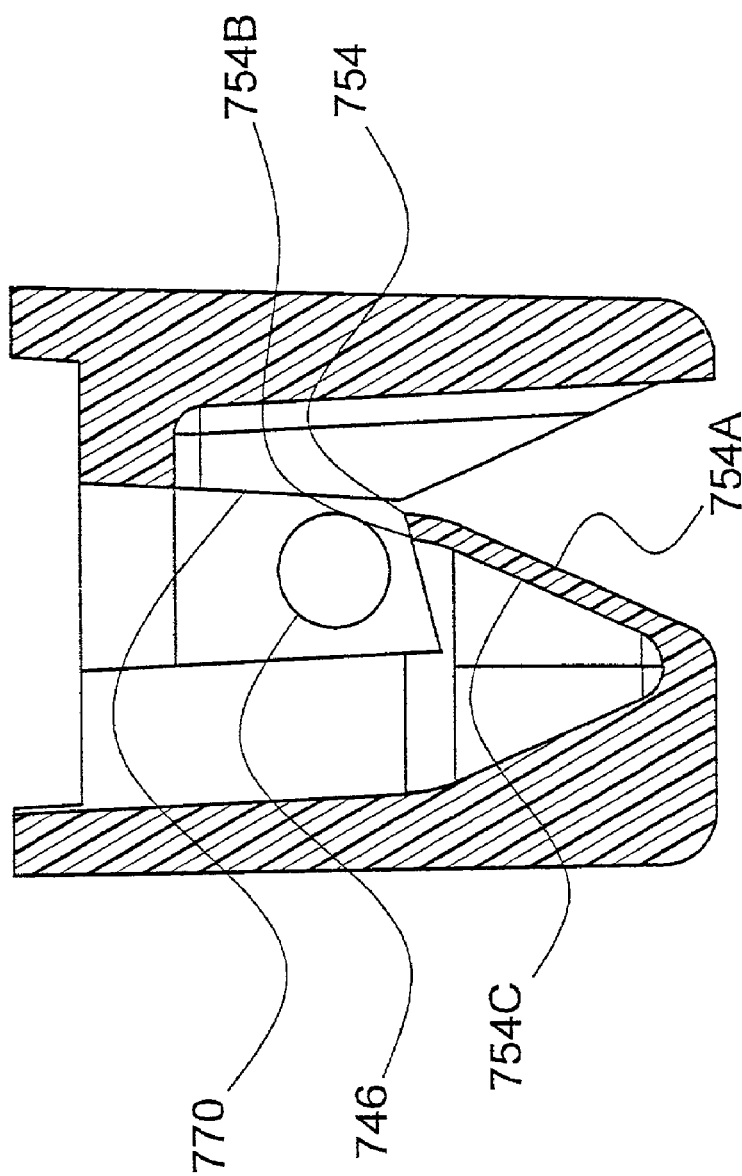
FIG. 26 is a cross-sectional view of the safety shield apparatus shown in FIG. 19 showing an embodiment of a needle latch.
Figure 27:
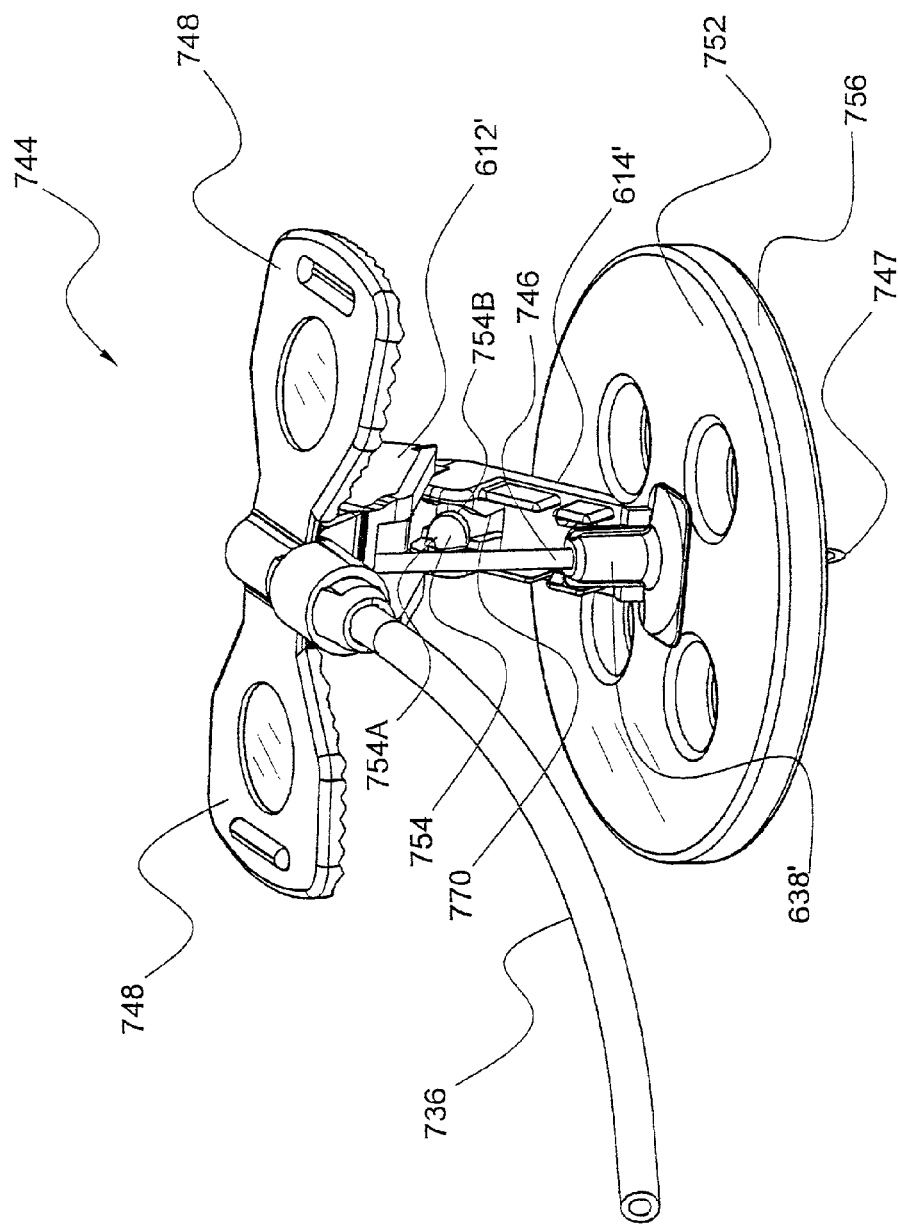
FIG. 27 is a rear view of the safety shield apparatus shown in FIG. 19 showing the needle latch shown in FIG. 26.

FIGS. 19 and 20 show safety shield apparatus 744 in a retracted position, while FIGS. 21 and 22 show the extended and protected position with shield 750 attached to needle 746 by means of a needle latch 754 shown in FIGS. 22, 26 and 27. Needle latch 754 has an arcuate outer surface 754A and a radial edge 754B. A deformable interior cavity 754C of latch 754 corresponds to outer surface 754A. Upon actuation of shield 750, needle 746 engages and travels along outer surface 754A until needle 754 becomes disposed over radial edge 754B. Outer surface 754A elastically deforms to facilitate movement of needle 746 thereover and extension of shield 750. Shield 750 is manipulated until the fully extended position is reached. Radial edge 754B prevents movement of needle 746 and consequently shield 750 to the retracted position, thereby locking shield 750 in the fully extended position. Movement of needle 746 is prevented due to the compressive forces created in outer surface 754A and tensile forces in 754B via engagement of needle 746 and radial edge 754B.

Figure 31:
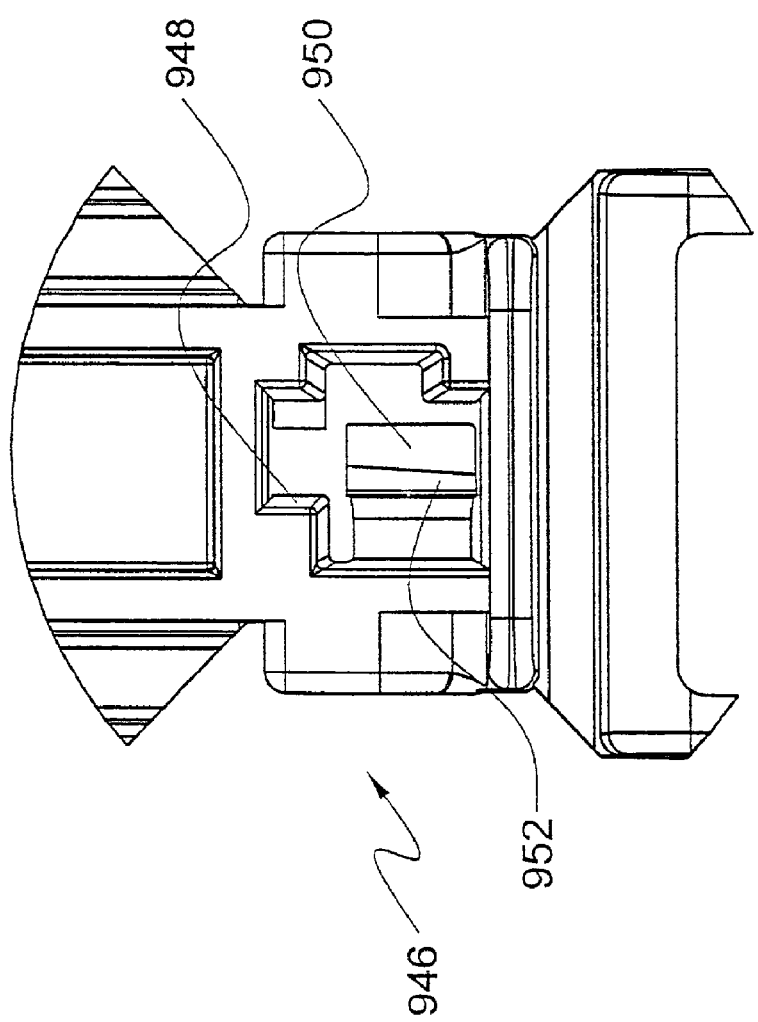
FIG. 31 is an enlarged bottom view of an alternate embodiment of a latch of the safety shield apparatus illustrated in FIG. 19.
Figure 32:
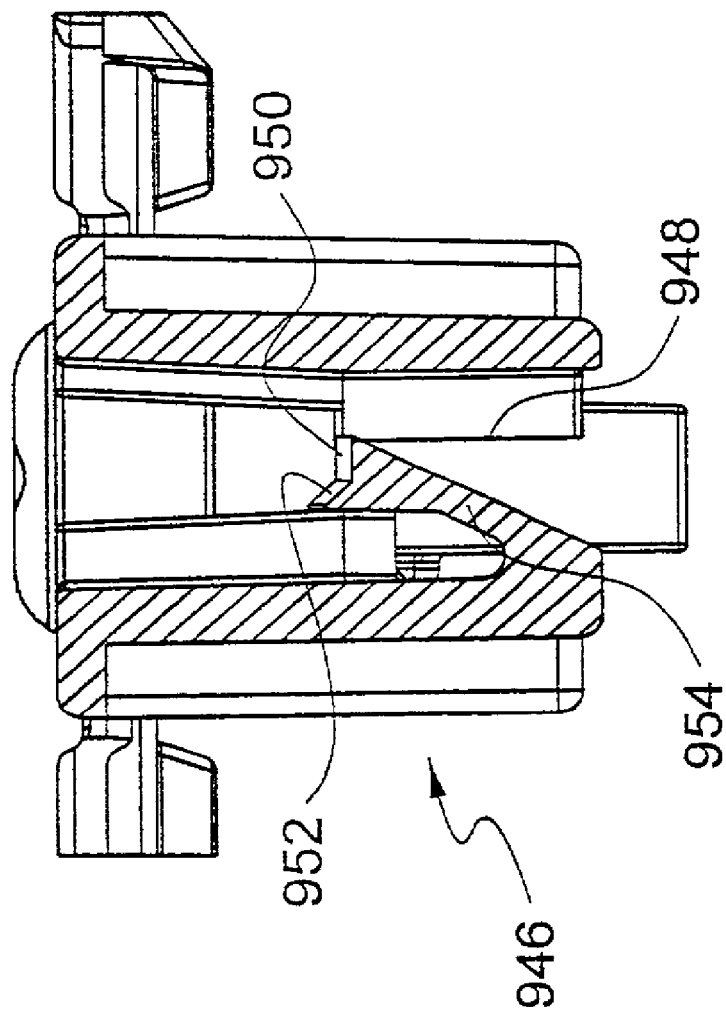
FIG. 32 is a side cross-sectional view of the latch illustrated in FIG. 31.

As shown in FIGS. 26 and 27, a rib 770 may be utilized for positioning the needle 746 with respect to needle latch 754. Needle 746 may be latched to shield 750 by various other means as set forth herein. For example, in an alternate embodiment, as shown in FIGS. 31 and 32, a needle latch 946 formed with shield 750. Needle latch 946 has a surface 950 on which needle 746 rests to lock shield 750 in the extended position. Surfaces 948 and 952 retain needle 746 with surface 950 in the locked and extended position. In operation, as shield 750 is manipulated to the fully extended position, needle 746 engages latch 946 and travels over latch arm 954, which biases permitting needle 746 to enter latch 946 and come to rest with surface 950. Latch arm 954 biases back, and in cooperation with surfaces 948, 952 retains needle 746, and correspondingly, shield 750 in the extended and locked position.

Shield 750 may further comprise a planar contact surface, such as, for example, disc 752 attached to linear bearing 638', which may be permanently attached or releasably attached. Linear bearing 638' may also be monolithically formed with disc 752. As shown in FIG. 20, linear bearing 638' defines a throughbore (no number) having an internal diameter that is substantially equal to the external diameter of needle 746. Disc 752. may further include foldable portions (not shown), such as by living hinges, for packaging purposes. Texturing may also be added to the top surface of disc 752 to enhance gripping of disc 752. Disc 752 may also be hingedly attached to distal segment 614' through hinge 782, thereby leaving linear bearing 638' free from communication with the disc 752. Linear bearing 638' remains connected to distal segment 14' through living hinge 78.

Figure 28:
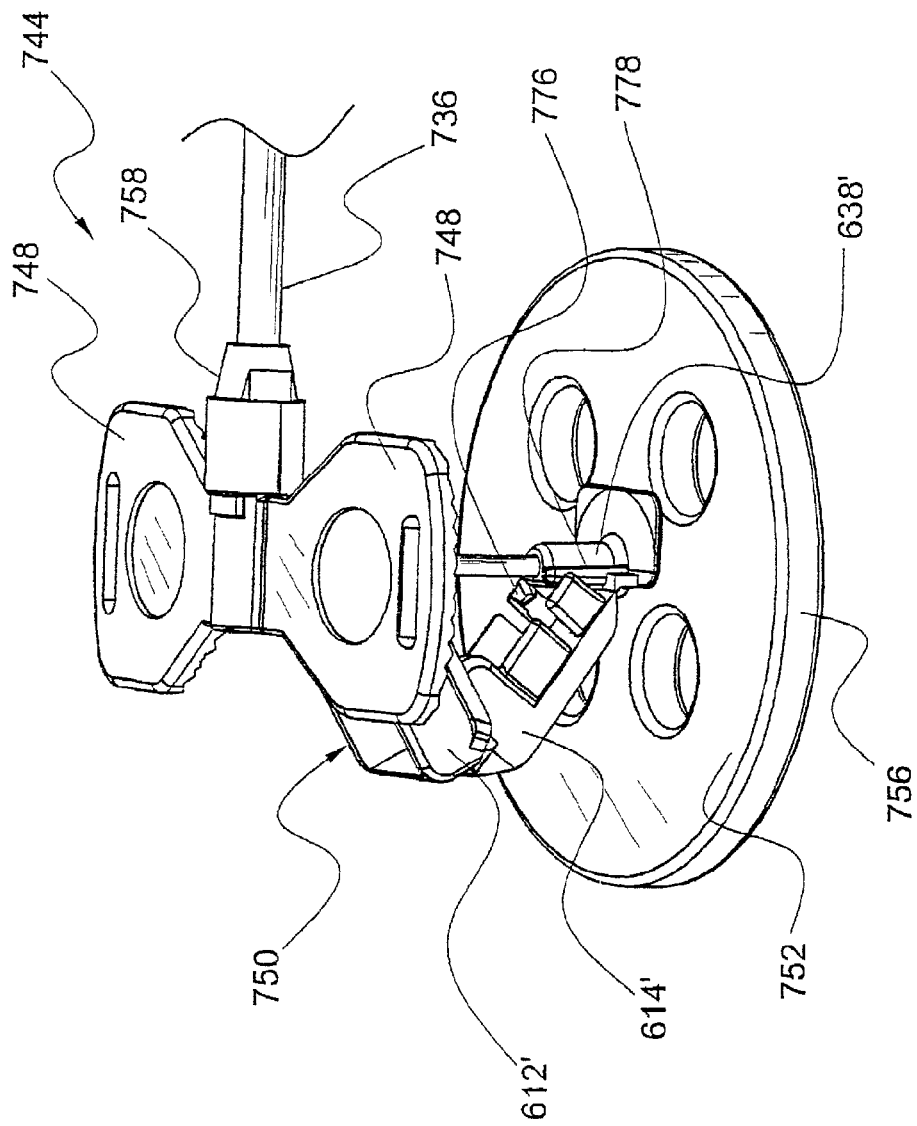
FIG. 28 is a perspective view of the safety shield apparatus shown in FIG. 19 showing an additional lockout feature.

Referring to the embodiment shown in FIG. 28, an additional lockout feature may be added for securing safety shield apparatus 744 in the lockout mode. For the embodiment shown in FIG. 28, the lockout is accomplished by engagement of latches 776 disposed on distal segment 614' to flanges 778 disposed on linear bearing 638'.

Shield 750 is passively activated upon withdrawal of the needle 746 from a patient, wherein wings 748 may be used to facilitate insertion and withdrawal of the safety shield apparatus 744. One method of withdrawing needle 746 from a patient includes the steps of holding disc 752 against a patient while pulling wings 748 away from the subject. Once the needle latch 754 engages the needle 746, the safety shield apparatus 744 may be removed. It is contemplated that disc 752 is adherently attached to the subject. Disc 752 may also be releasable from linear bearing 638'.

The hinges connecting segments 612' and 614' and linear bearing 638' may be flexible living hinges 678, pinned hinges, or equivalents thereof that provide for hinged connections of segments 612' and 614' and the linear bearing 638' (see, e.g., FIG. 26). Moreover, the number of hingedly connected segments depends upon needle 746 length and device length required to extend shield 744 beyond distal end 747 of needle 746. Embodiments of the safety shield apparatus 744 may, therefore, include two or more segments.

Figure 33:
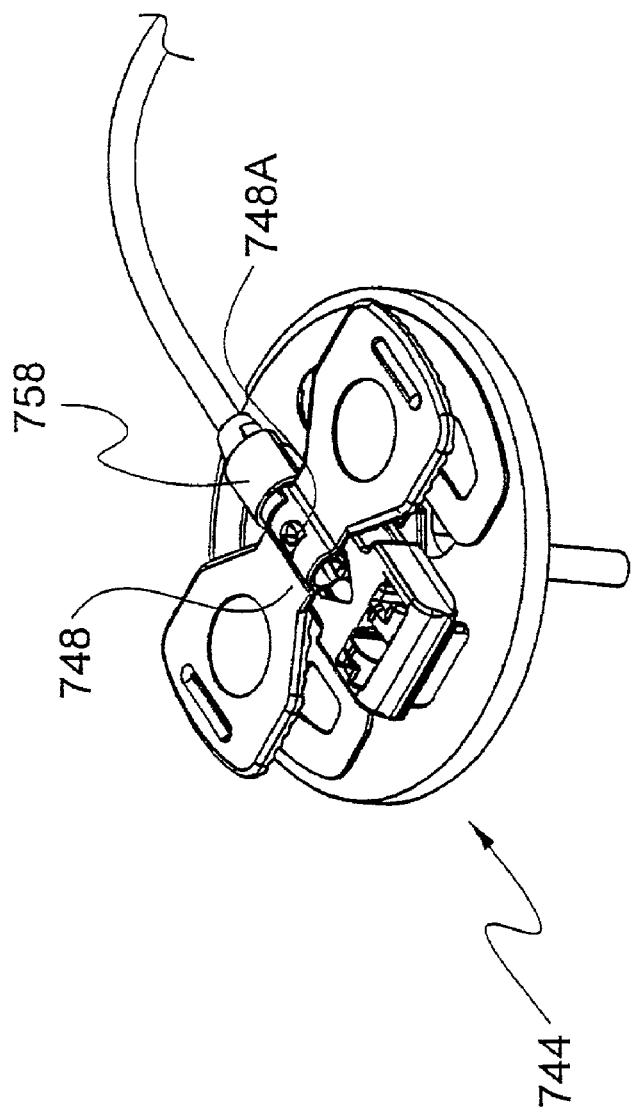
FIG. 33 is a perspective view of another alternate embodiment of the safety shield apparatus.

As shown in the embodiment illustrated in FIG. 19, needle 746 has a proximal end and a distal end 747 with the proximal end of needle 746 affixed in a hub 758. Wings 748 may be affixed to the needle hub. In the embodiment shown in FIG. 25, safety shield apparatus 744 is assembled by inserting hub 758 into collar 760. Flared surfaces 762 may be included on hub 758 to engage collar 760. The needle hub may also be configured to attach an extension set tubing 736. In an alternate embodiment, as shown in FIG. 33, needle hub 758 and wings 748 include an opening 748A. Opening 748A permits linear bearing 638' (see, e.g., FIG. 26) to extend farther into needle hub 758 and wings 748, and form a friction fit therewith, such that shield 750 can be maintained in the retracted position, as shown. This configuration advantageously provides greater stability and increased coverage of needle 746.

Figure 23:
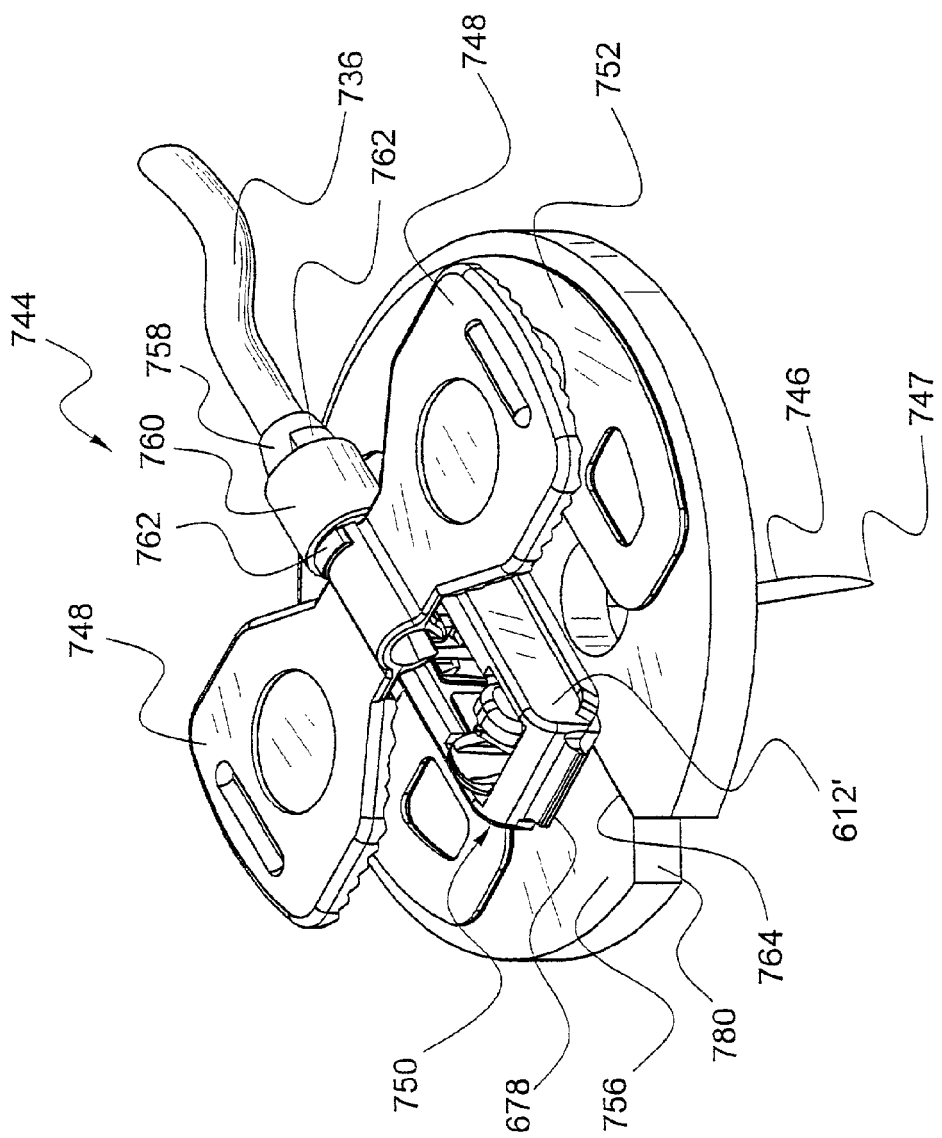
FIG. 23 is a perspective view of the safety shield apparatus shown in FIG. 19 in a retracted position showing an alternate embodiment of a linear bearing with a foam disc.
Figure 24A:
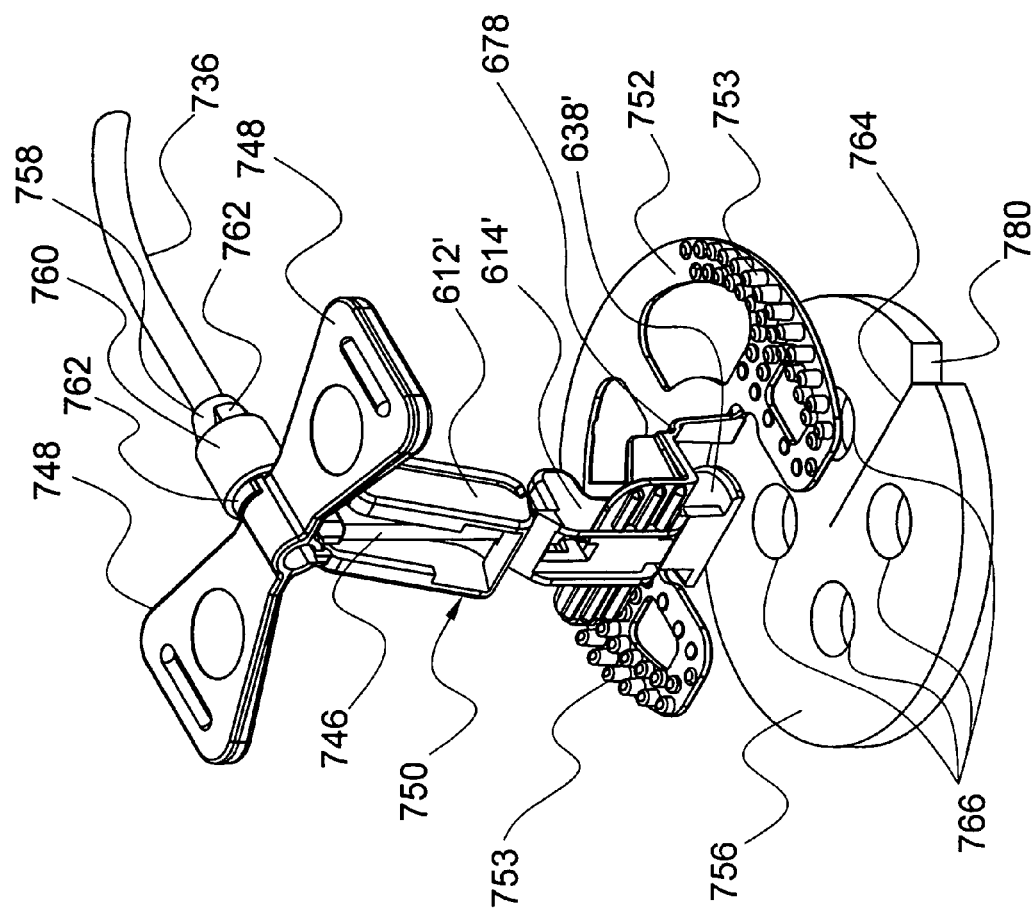
FIG. 24 is a perspective view of the safety shield apparatus shown in FIG. 23 fully extended and having the foam disc separated.
Figure 25A:
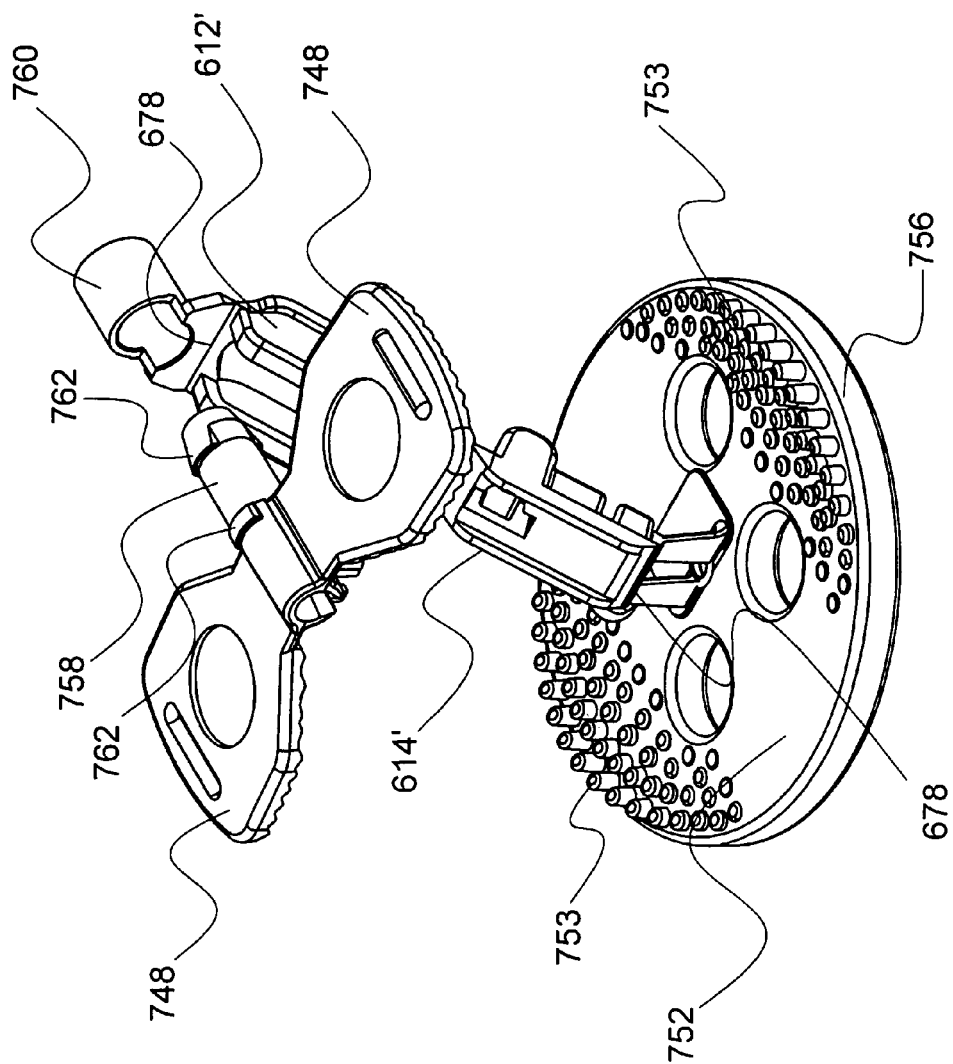
FIG. 25 is a perspective view of the safety shield apparatus shown in FIG. 19 showing an alternate embodiment of a linear bearing and the shield separated from the needle hub and wing assembly.

Referring to FIGS. 23 and 24, an embodiment of safety shield apparatus 744 is shown farther comprising a pad 756, which may be added underneath disc 752 for patient comfort and as a spacer between a patient's skin and disc 752. Pad 756 may be comprised of a foam material such as a closed-cell foam, polyurethane open-cell foam, or an equivalent crushed or densified, felted material. Pad 756 may be an absorbent, breathable material that may also be capable of wicking moisture. Pad 756 may also be impregnated with an antimicrobial agent, such as chlorhexidine or equivalent material. Pad 756 may also be comprised of a foam material with a thin film coating on either side including, but not limited to, polyolefin, breathable polyurethane, or other equivalent materials. The thin film coating may also be perforated.

Pad 756 may be separately packaged in a sterile container for use as a replacement pad for an existing dressing. Pad 756 may also be used as a dressing, which may replace or supplement a gauze dressing.

Pad 756 may have a friction fit capability for attachment to needle 746, with a possible slit 764 included for ease of attachment to safety shield apparatus 744. Pad 756 may also be permanently attached to safety shield apparatus 744. A notch 780 may be added to slit 764 to assist in guiding the pad 756 into the proper position on the needle 746. Holes 766 may be added to the pad 756 for purposes such as aiding in visibility and increasing air flow to the pad 756. Similar holes may be added to the disc 752 for the same purposes.

Figure 29:
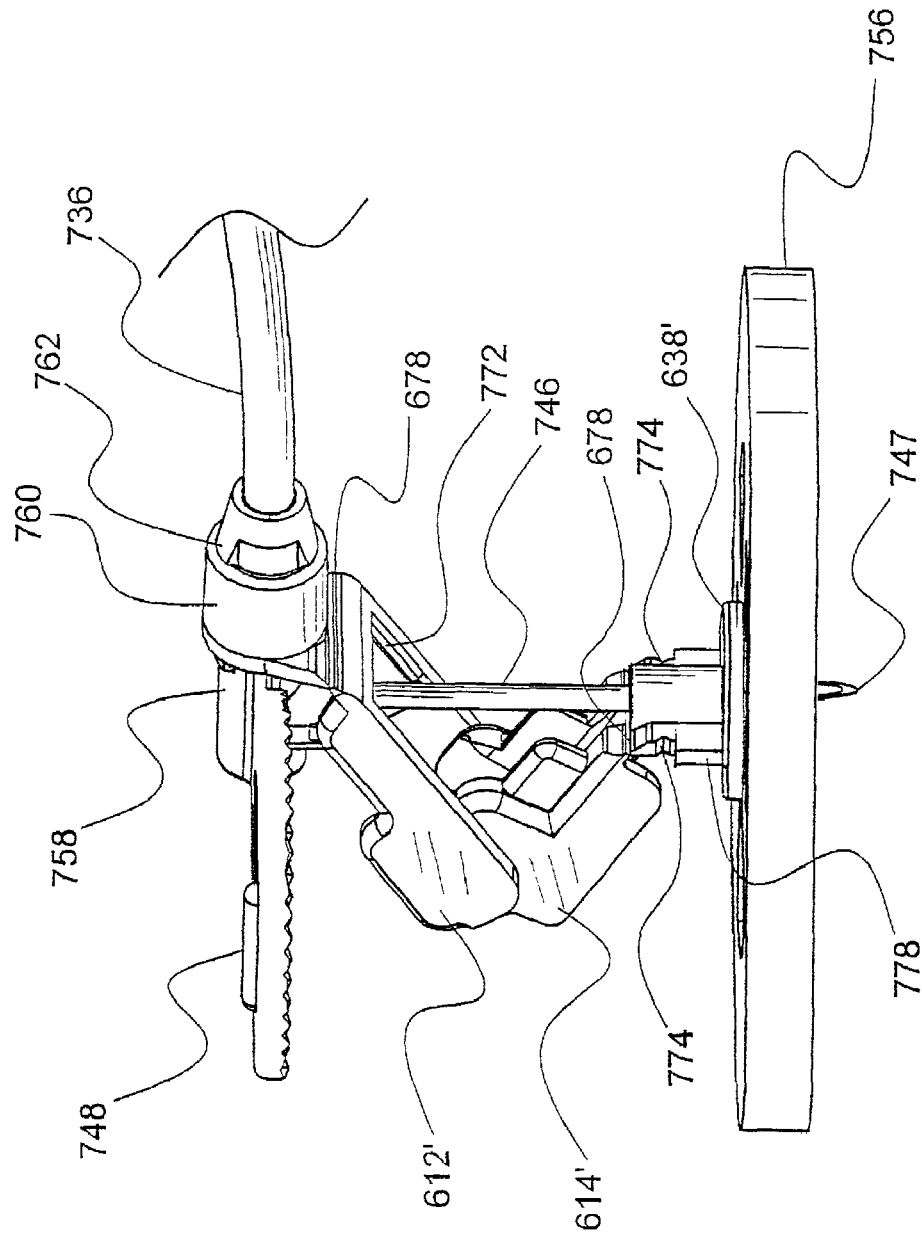
FIG. 29 is a perspective view of the safety shield apparatus shown in FIG. 19 illustrating an embodiment of a latch for retaining the safety shield apparatus in a retracted position.
Figure 30:
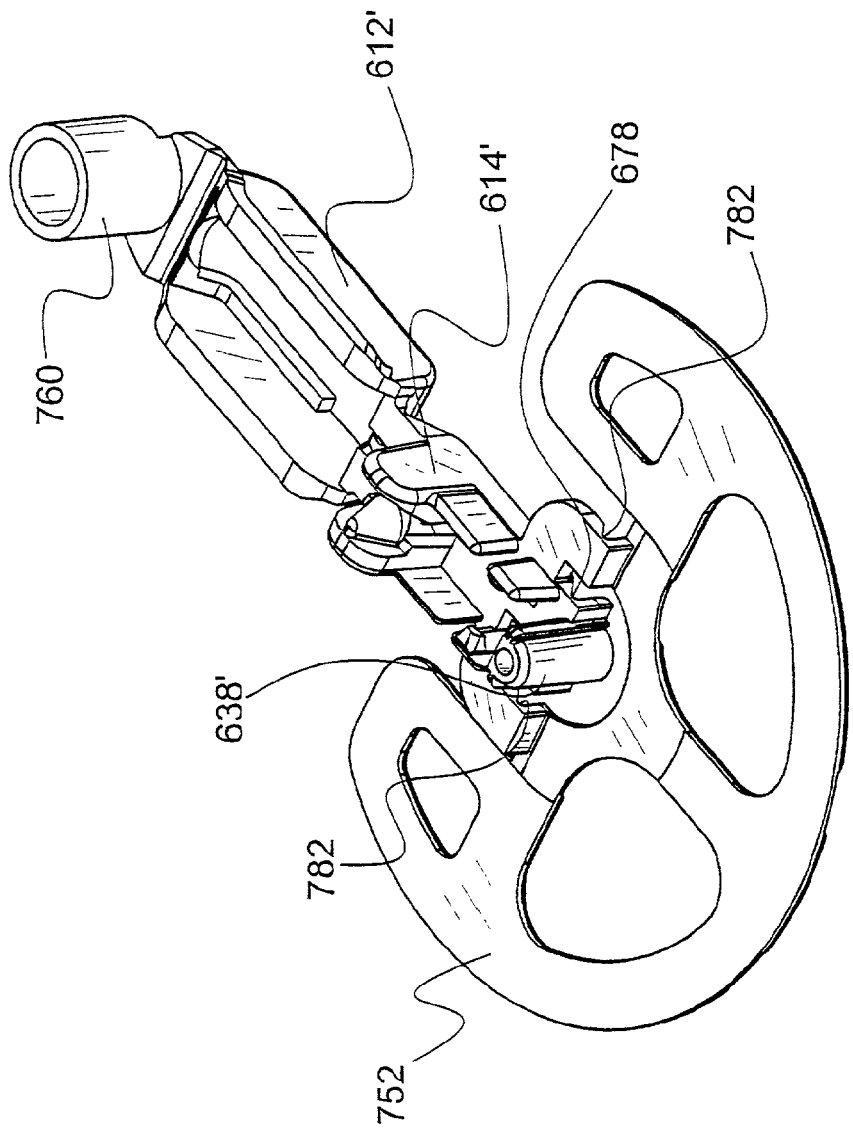
FIG. 30 is a perspective view of the safety shield apparatus shown in FIG. 19 showing an alternate embodiment of a disc.

Referring to the embodiment shown in FIG. 29, safety shield apparatus 744 may be retained in the retracted position by a flange 772 disposed on proximal segment 612' engaging notches 774 in a flange 778 disposed on linear bearing 638'. Alternative embodiments may include a flange disposed on the hub 758 or distal segment 674' with corresponding notches located on an alternate segment or hub 758.

Referring to FIG. 34, another alternate embodiment of a safety shield apparatus 810, in accordance with the principles of the present disclosure, similar to the apparatus and methods of use of safety shield apparatus 10, 10", 310 and 744 described above, is shown. Safety shield apparatus 810 includes a port access medical needle 820, a needle hub assembly 830, a shield assembly 840 of hingedly connected segments 842 and 844 for protecting a distal portion 860 of needle 820, and a section of medical tubing 50. Medical needle 820 has a linear shaft extending along a longitudinal axis c and a distal portion 860 and a proximal portion 880. Proximal portion 880 is mounted to needle hub assembly 830. The channel of fluid flow 852 in hub assembly 830 may be angled such that a relatively straight needle 820 may be utilized, rather than an angled needle as heretofore shown.

FIG. 34 shows safety shield apparatus 810 in the extended and protected position with shield 840 attached to needle 820 by means of a needle latch 846, similar to the needle latches described above.

Shield assembly 840 may further comprise a planar contact surface, such as, for example, disc 848 attached to linear bearing 850, which may be permanently attached or releasably attached. Linear bearing 850 may also be monolithically formed with disc 848. Shield assembly 840 is extensible between a retracted position and an extended position, similar to the embodiments described above, via fixed positioning of disc 848.

In another embodiment, the hub may be configured to include a luer fitting for attachment to various needle devices such as a syringe or IV set.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A safety shield apparatus comprising:
   a needle having a distal portion defining a longitudinal axis which is angularly displaced relative to a longitudinal axis defined by a proximal portion of the needle; and
   a shield including at least one elongated part, the shield having a proximal end mounted with the proximal portion of the needle and a distal end mounted with a planar contact surface, the planar contact surface including a plurality of openings and a needle linear bearing that slidably engages the needle to facilitate movement of the needle relative to the shield, the shield being extensible between a retracted position and an extended position via fixed positioning of the planar contact surface relative to movement of the shield.

2. A safety shield apparatus according to claim 1, wherein the planar contact surface includes an anchor part.

3. A safety shield apparatus according to claim 1, wherein the distal end of the shield is hingedly attached to the planar contact surface.

4. A safety shield apparatus according to claim 1, wherein the planar contact surface includes a pad for engagement with a subject.

* * * * *